(12) United States Patent
Naseri et al.

(10) Patent No.: US 10,973,496 B2
(45) Date of Patent: Apr. 13, 2021

(54) COLLECTION DEVICE FOR DIAGNOSTICS OF VAGINAL DISCHARGE

(71) Applicant: Qurasense, Inc., Palo Alto, CA (US)

(72) Inventors: Sara Naseri, Stanford, CA (US); Søren Therkelsen, Woodside, CA (US)

(73) Assignee: QURASENSE, INC., Palo Alto, CA (US)

(*) Notice: Subject to any disclaimer, the term of this patent is extended or adjusted under 35 U.S.C. 154(b) by 312 days.

(21) Appl. No.: 16/085,932

(22) PCT Filed: Mar. 20, 2017

(86) PCT No.: PCT/US2017/023246
§ 371 (c)(1),
(2) Date: Sep. 17, 2018

(87) PCT Pub. No.: WO2017/161378
PCT Pub. Date: Sep. 21, 2017

(65) Prior Publication Data
US 2019/0099166 A1 Apr. 4, 2019

Related U.S. Application Data

(60) Provisional application No. 62/310,209, filed on Mar. 18, 2016.

(51) Int. Cl.
*A61B 5/00* (2006.01)
*A61B 10/00* (2006.01)
(Continued)

(52) U.S. Cl.
CPC ...... *A61B 10/0045* (2013.01); *A61B 10/0291* (2013.01); *A61F 13/15* (2013.01);
(Continued)

(58) Field of Classification Search
CPC ............ A61B 10/0045; A61B 10/0074; A61B 10/0291; A61F 13/15; A61F 13/53;
(Continued)

(56) References Cited

U.S. PATENT DOCUMENTS 4,628,941 A 12/1986 Kosasky
4,800,896 A 1/1989 Jalowayski
(Continued)

FOREIGN PATENT DOCUMENTS

DE 19837678 A1 3/2000
JP 2002-542843 A 12/2002
(Continued)

OTHER PUBLICATIONS

Extended European Search Report issued in EP 17767708.5, dated Feb. 4, 2019 (8 pages).
(Continued)

*Primary Examiner* — Max F Hindenburg
(74) *Attorney, Agent, or Firm* — Epstein Drangel LLP; Robert L. Esptein

(57) ABSTRACT

A method of analyzing vaginal fluid includes collecting vaginal fluid in a vaginal fluid collecting system and transporting the collected vaginal fluid to a location for analysis. The analysis can be stored in and retrieved from a secure cloud storage data base.

50 Claims, 27 Drawing Sheets

(51) Int. Cl.
A61F 13/535 (2006.01)
A61F 13/84 (2006.01)
A61F 13/472 (2006.01)
G01N 33/52 (2006.01)
A61F 13/15 (2006.01)
A61B 10/02 (2006.01)

(52) U.S. Cl.
CPC .......... *A61F 13/472* (2013.01); *A61F 13/535* (2013.01); *A61F 13/84* (2013.01); *G01N 33/525* (2013.01); *A61B 2010/0074* (2013.01); *A61F 2013/8473* (2013.01); *G01N 2333/025* (2013.01)

(58) Field of Classification Search
CPC ...... A61F 13/84; A61F 13/472; A61F 13/535; G01N 33/525
See application file for complete search history.

(56) References Cited

U.S. PATENT DOCUMENTS

| | | | |
|---|---|---|---|
| 4,953,563 | A | 9/1990 | Kaiser et al. |
| 5,063,930 | A | 11/1991 | Nucci |
| 5,259,391 | A | 11/1993 | Altshuler et al. |
| 5,300,054 | A * | 4/1994 | Feist ................ A61F 13/15203 604/358 |
| 5,735,801 | A | 4/1998 | Caillouette |
| 5,827,200 | A | 10/1998 | Caillouette |
| 5,916,176 | A | 6/1999 | Caillouette |
| 6,007,498 | A | 12/1999 | Buck et al. |
| 6,013,036 | A | 1/2000 | Caillouette |
| 6,019,734 | A | 2/2000 | Parkinson |
| 6,063,042 | A | 5/2000 | Navot et al. |
| 6,126,597 | A | 10/2000 | Smith et al. |
| 6,149,590 | A | 11/2000 | Smith et al. |
| 6,352,513 | B1 | 3/2002 | Anderson et al. |
| 6,390,991 | B1 | 5/2002 | Caillouette |
| 6,409,681 | B1 | 6/2002 | Caillouette |
| 6,475,165 | B1 | 11/2002 | Fournier |
| 7,458,941 | B2 | 12/2008 | Caillouette |
| 7,666,148 | B1 | 2/2010 | Caillouette |
| 7,771,366 | B2 | 8/2010 | Kirsner |
| 7,947,467 | B2 | 5/2011 | Kritzman et al. |
| 8,734,364 | B1 | 5/2014 | Mantzaris et al. |
| 8,911,988 | B2 | 12/2014 | Miller |
| 9,017,267 | B2 * | 4/2015 | Okada ................ A61B 5/14532 600/573 |
| 9,110,053 | B2 | 8/2015 | Cohen et al. |
| 2001/0023321 | A1 | 9/2001 | Gombrich et al. |
| 2002/0007161 | A1 | 1/2002 | Bouchard et al. |
| 2002/0032389 | A1 | 3/2002 | Fournier |
| 2002/0058886 | A1 | 5/2002 | Caillouette |
| 2003/0017605 | A1 | 1/2003 | Kritzman et al. |
| 2003/0028123 | A1 | 2/2003 | Pevoto |
| 2003/0166293 | A1 | 9/2003 | Kritzman et al. |
| 2004/0068162 | A1 | 4/2004 | Kirsner |
| 2004/0106190 | A1 | 6/2004 | Yang et al. |
| 2004/0220538 | A1 | 11/2004 | Panopoulos |
| 2007/0003993 | A1 | 1/2007 | Kritzman et al. |
| 2007/0047568 | A1 | 3/2007 | Wang et al. |
| 2007/0073192 | A1 | 3/2007 | Caillouette |
| 2008/0009769 | A1 | 1/2008 | Caillouette |
| 2008/0077097 | A1 | 3/2008 | Chambers et al. |
| 2008/0269706 | A1 | 10/2008 | Long et al. |
| 2009/0017474 | A1 | 1/2009 | Maltzman et al. |
| 2010/0222708 | A1 | 9/2010 | Hitchcock et al. |
| 2011/0190595 | A1 | 8/2011 | Bennett et al. |
| 2011/0230743 | A1 | 9/2011 | Inciardi et al. |
| 2012/0040655 | A1 | 2/2012 | Larkin |
| 2012/0085645 | A1 | 4/2012 | Mousa et al. |
| 2012/0130195 | A1 | 5/2012 | Martin et al. |
| 2012/0206265 | A1 | 8/2012 | Solazzo et al. |
| 2013/0053657 | A1 | 2/2013 | Ziarno et al. |
| 2013/0165816 | A1 | 6/2013 | Mor |
| 2013/0254141 | A1 | 9/2013 | Barda et al. |
| 2013/0289443 | A1 | 10/2013 | Kim et al. |
| 2013/0296739 | A1 | 11/2013 | Schultz |
| 2013/0331666 | A1 | 12/2013 | Miller |
| 2014/0066807 | A1 | 3/2014 | Lundkvist et al. |
| 2014/0121473 | A1 | 5/2014 | Banet et al. |
| 2014/0121487 | A1 | 5/2014 | Faybishenko et al. |
| 2014/0198203 | A1 | 7/2014 | Vardi et al. |
| 2014/0200538 | A1 | 7/2014 | Euliano et al. |
| 2014/0330167 | A1 | 11/2014 | Speck et al. |

FOREIGN PATENT DOCUMENTS

| | | |
|---|---|---|
| JP | 2009-512858 A | 3/2009 |
| JP | 2010-502249 A | 1/2010 |
| JP | 2010-531169 A | 9/2010 |
| JP | 2013-522650 A | 6/2013 |
| TW | 476640 | 2/2002 |
| WO | WO-0000233 A1 | 1/2000 |
| WO | WO-0065348 A2 | 11/2000 |
| WO | WO-2011119644 A1 | 9/2011 |
| WO | WO-2012019214 A1 | 2/2012 |
| WO | WO-2012126507 A1 | 9/2012 |
| WO | WO-2013097899 A1 | 7/2013 |
| WO | WO-2013152087 A2 | 10/2013 |

OTHER PUBLICATIONS

Extended European Search Report issued in EP15834024.0, dated Mar. 13, 2018 (8 pages).

International Search Report and Written Opinion issued by the U.S. Patent and Trademark Office as International Searching Authority for International Application No. PCT/US15/43883 dated Nov. 12, 2015 (13 pages).

International Search Report and Written Opinion issued by the U.S. Patent and Trademark Office as International Searching Authority in International Application No. PCT/US17/23246, dated Jul. 26, 2017 (17 pages).

\* cited by examiner

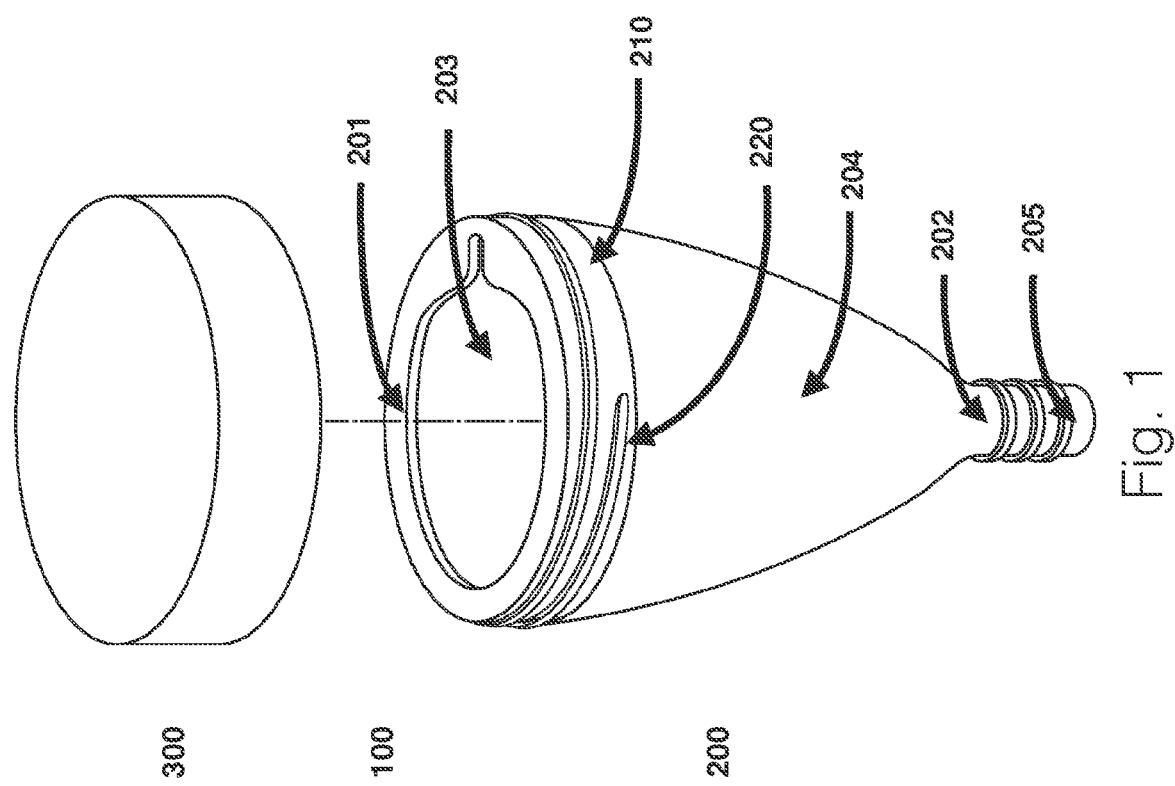

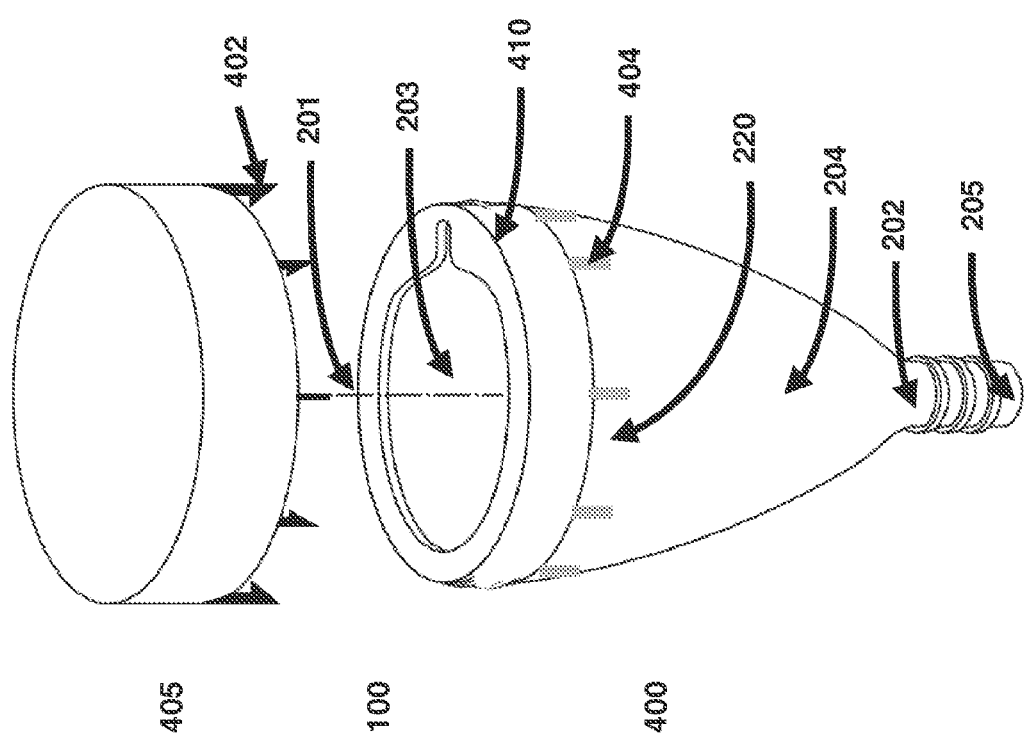

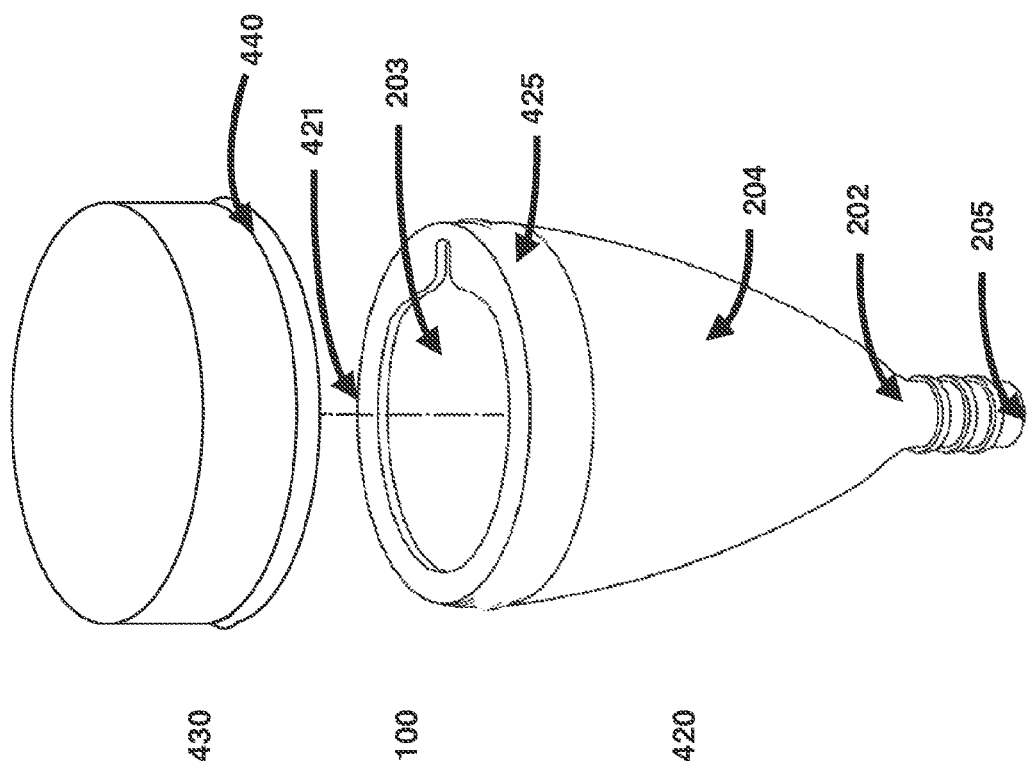

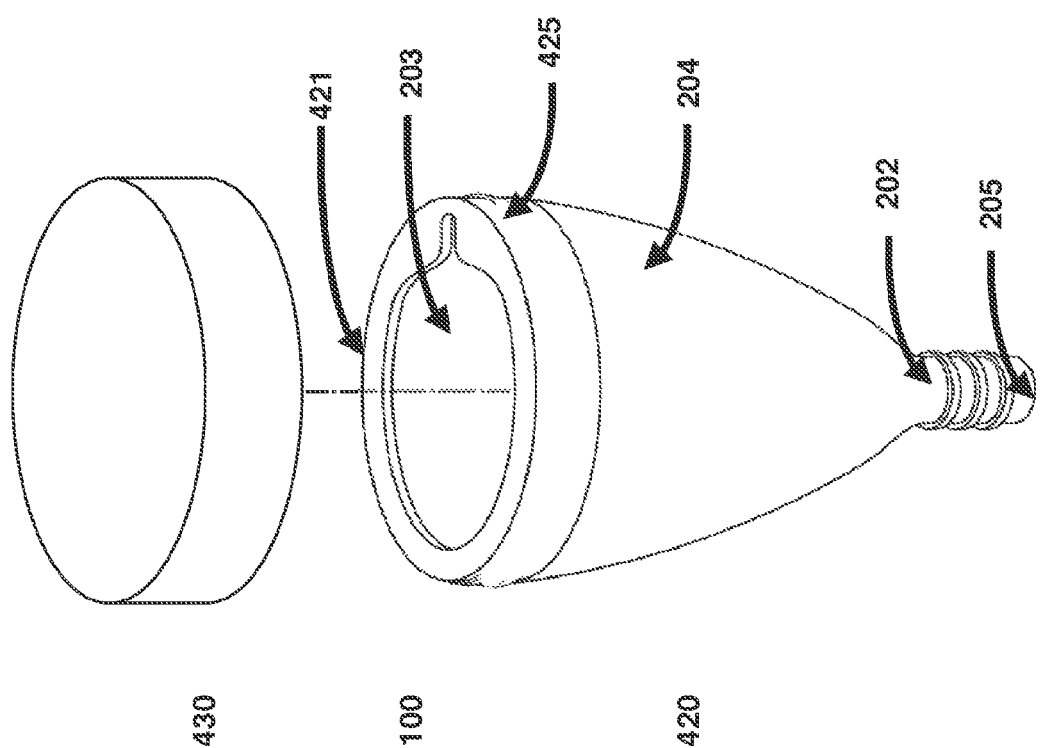

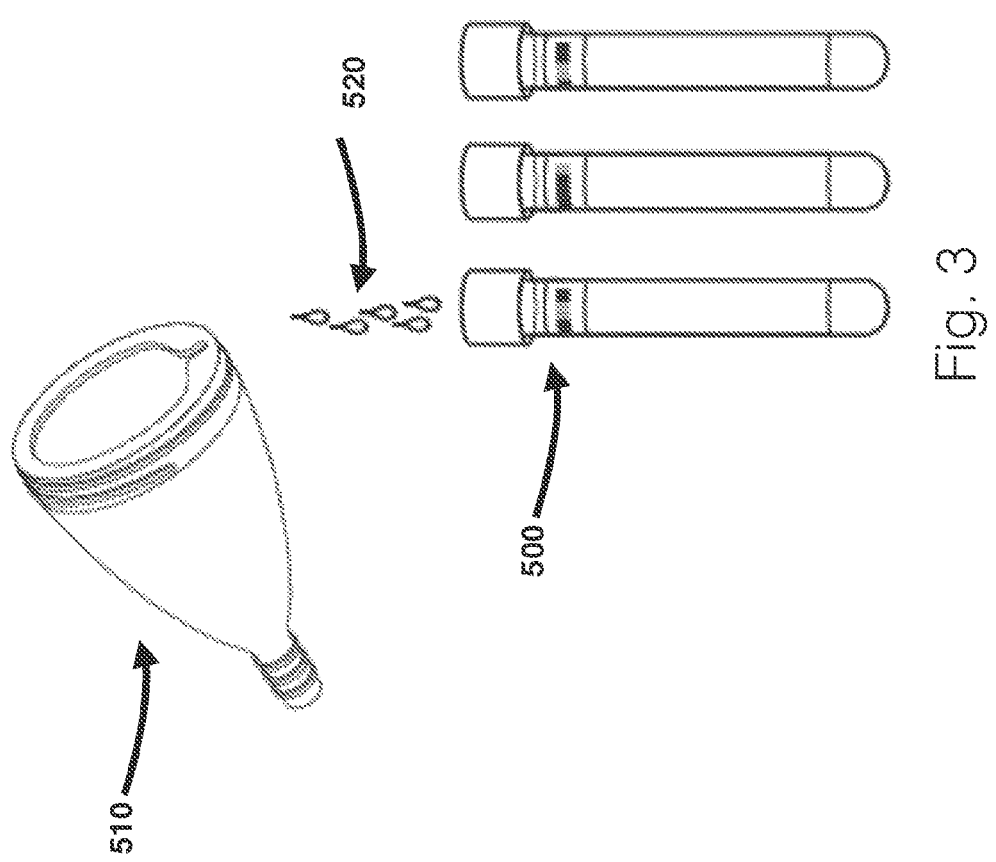

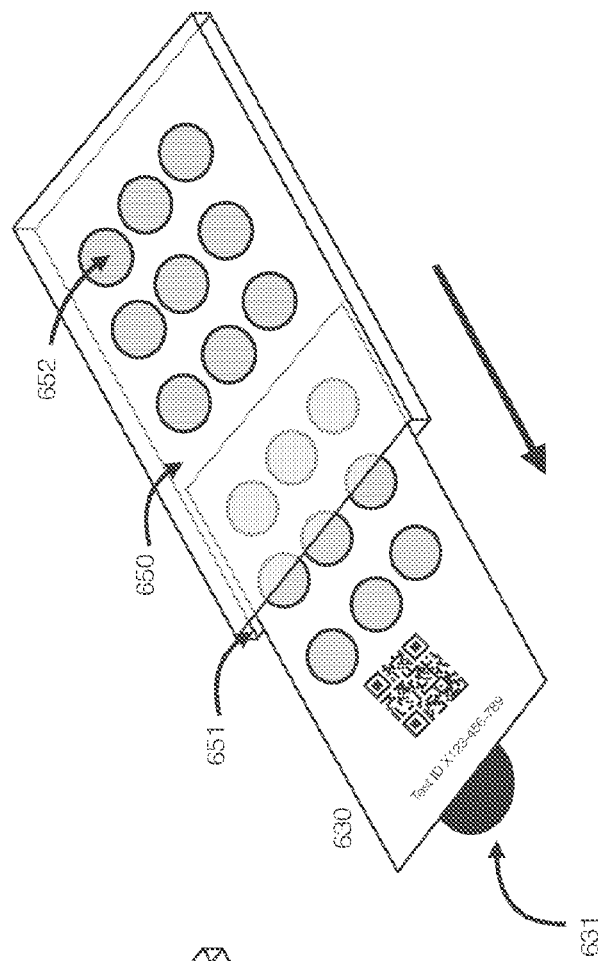
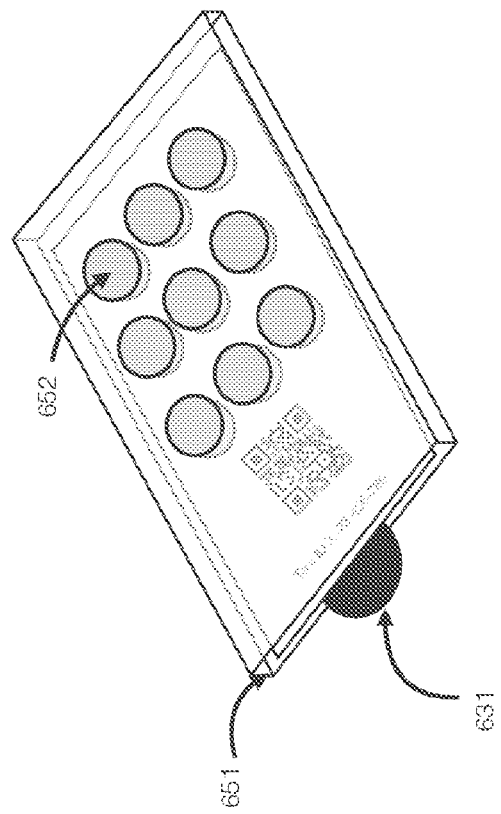
Fig. 5B

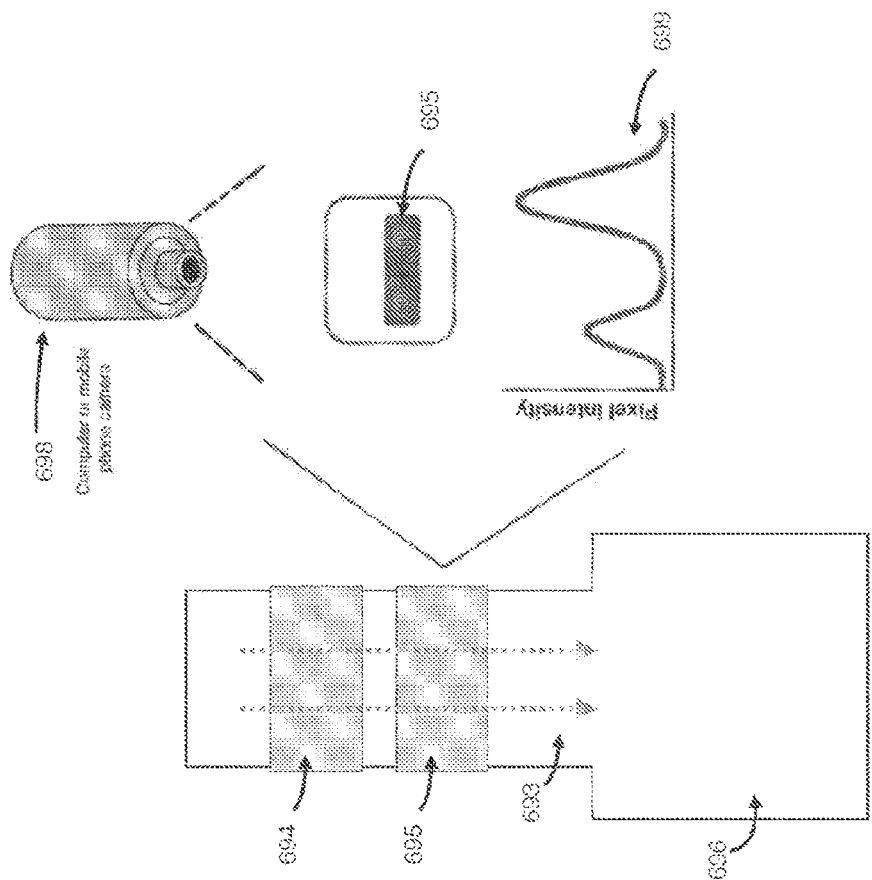
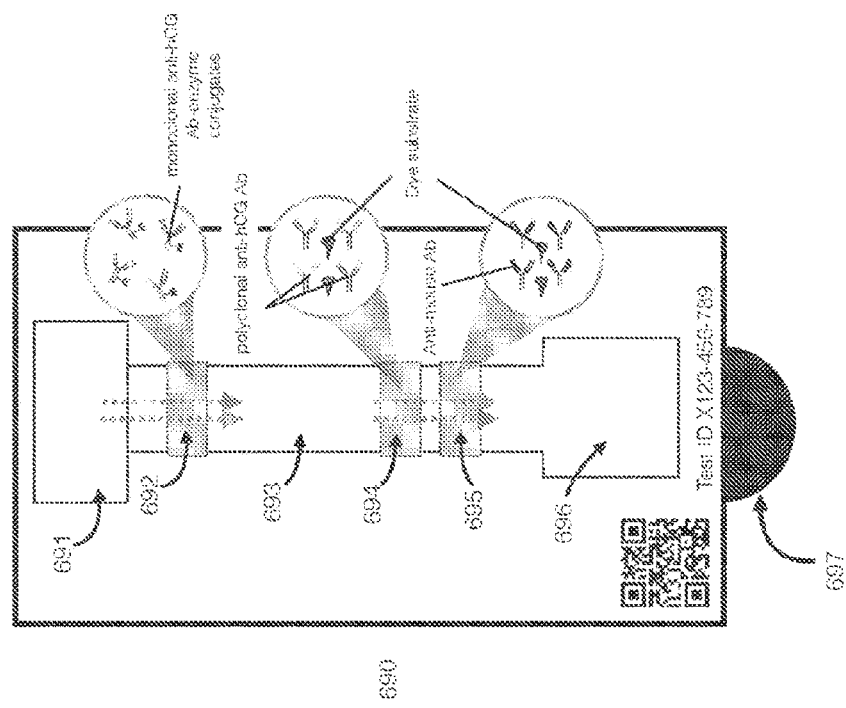
Fig 5D
Fig 5C

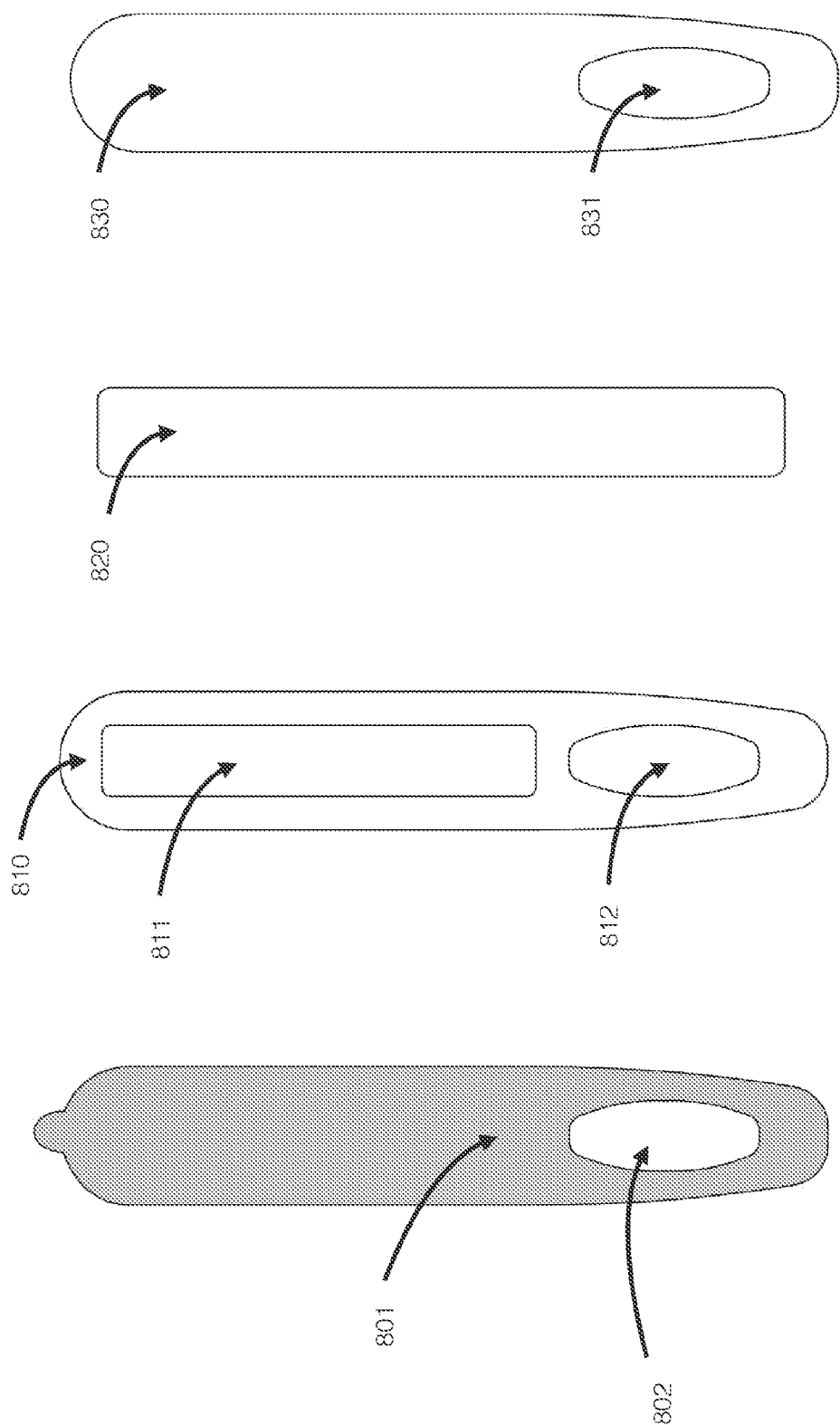

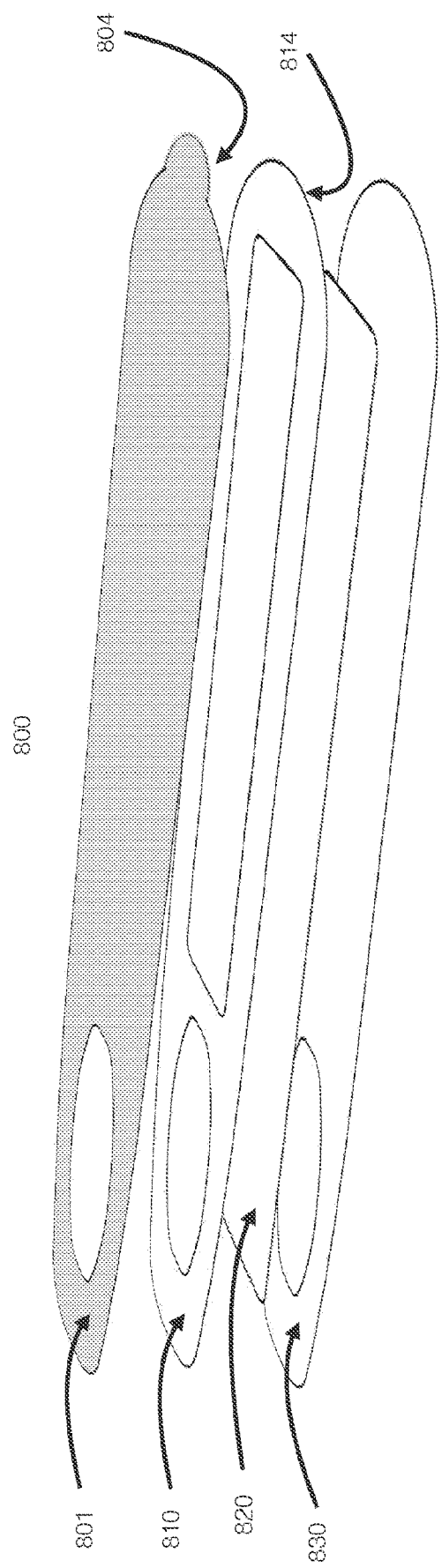

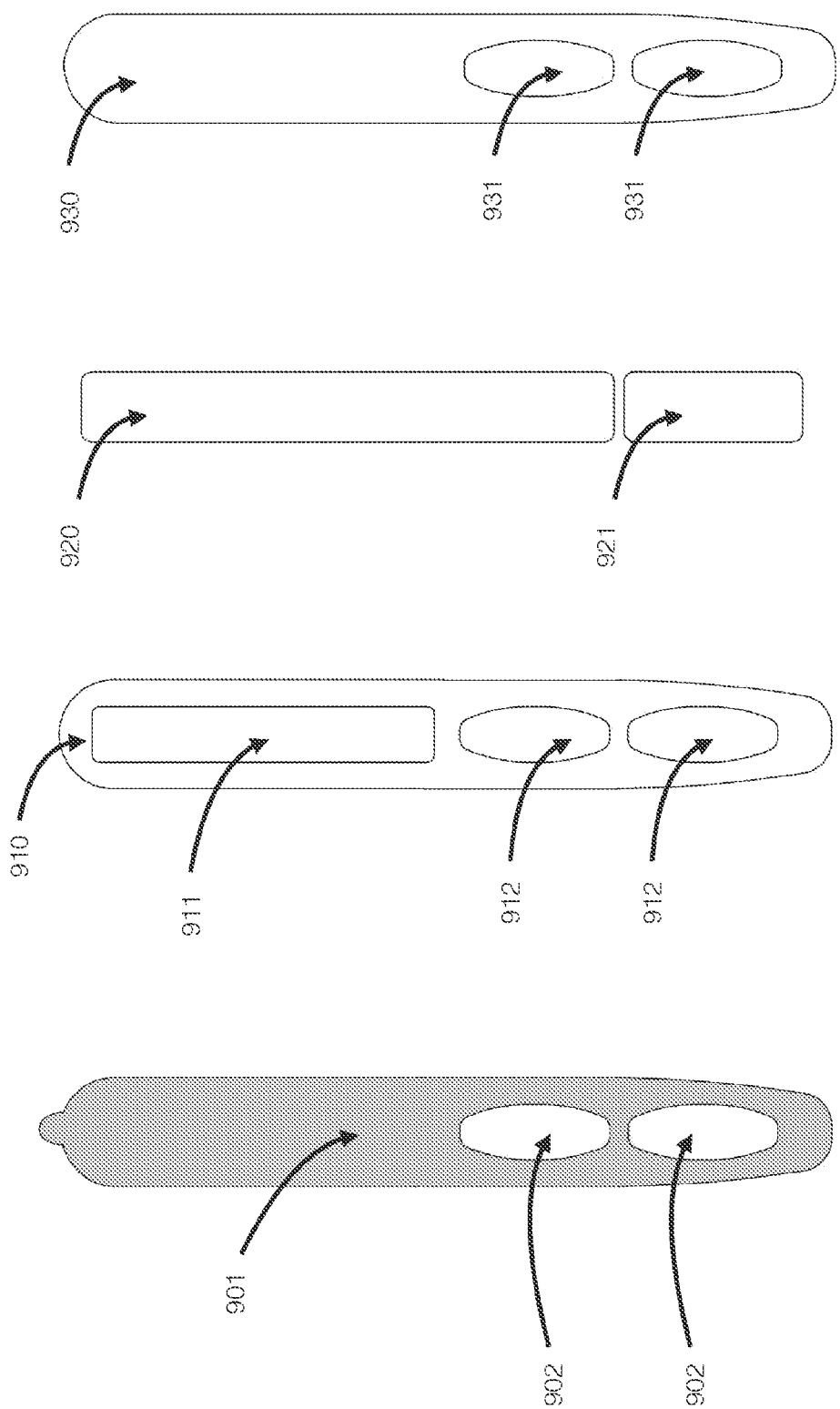

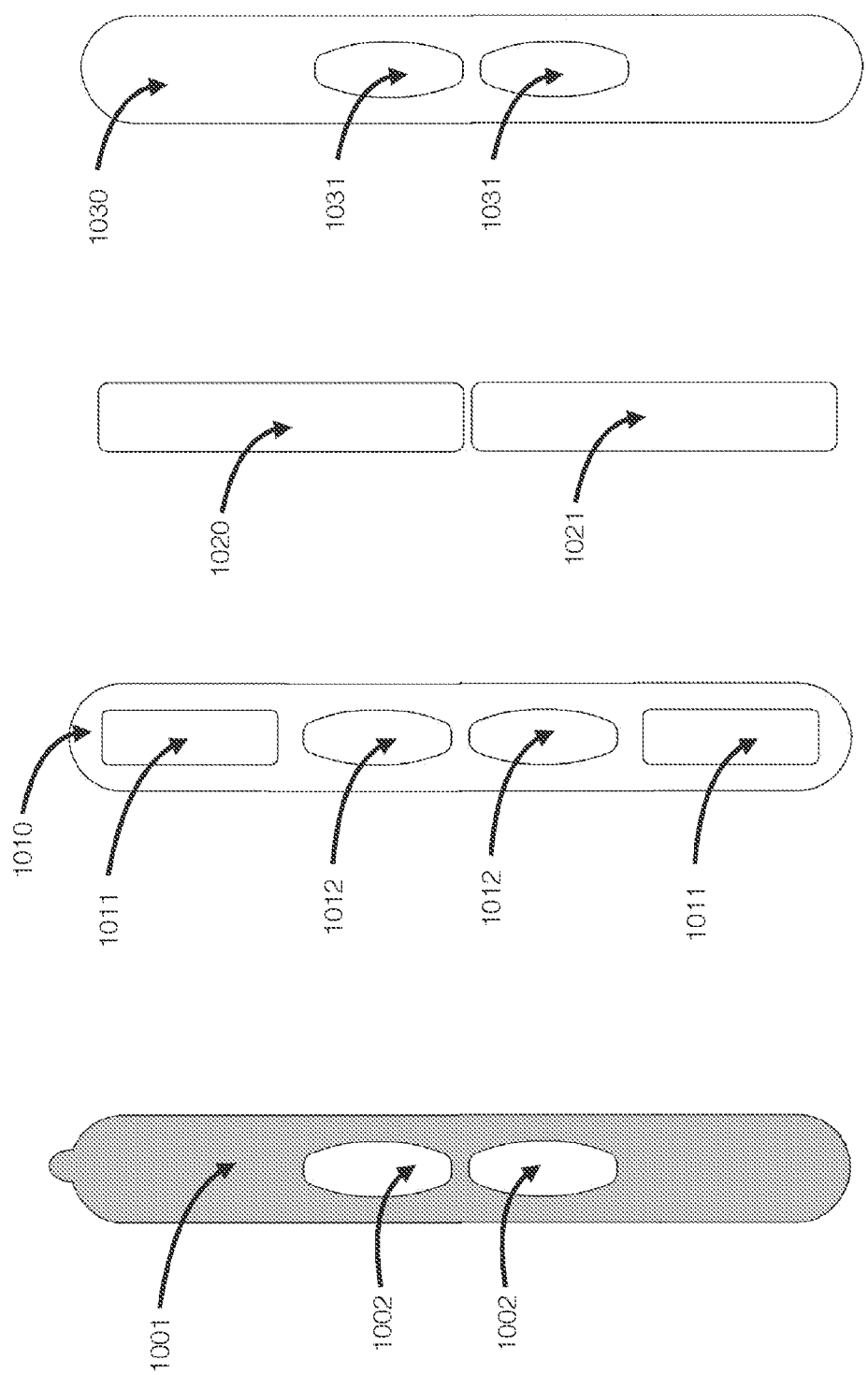

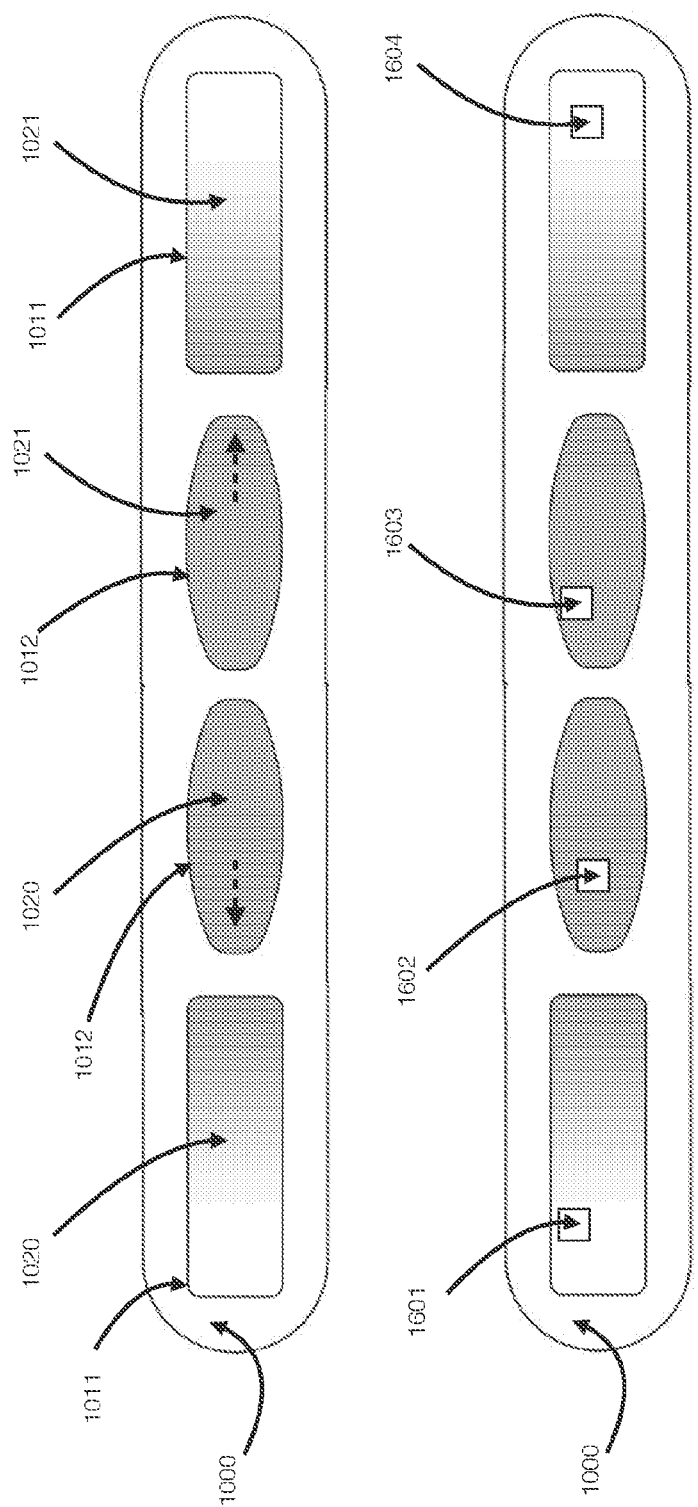

COLLECTION DEVICE FOR DIAGNOSTICS OF VAGINAL DISCHARGE

This application is a National Stage Entry of PCT International Application No. PCT/US2017/023246 filed on Mar. 20, 2017 which claims the benefit of priority under 35 C.F.R. § 119(e) to U.S. Patent Application No. 62/310,209, filed on Mar. 18, 2016, the content of which is incorporated by reference herein by its entirety.

BACKGROUND

Field of the Invention

The present invention relates to menstrual blood and vaginal discharge collection for the purpose of menstrual blood and vaginal discharge diagnostics.

Description of the Related Art

Currently, the only way to access systemic blood for diagnostic analysis is through invasive procedures such as a blood draw using a syringe, or a finger prick stick. For endometrial tissue analysis, one has to get a biopsy or a scrape from the cervix, which is both an invasive procedure and an uncomfortable experience. Both endometrial tissue and systemic blood contain important biomarkers used for diagnostics in women health, yet both collection methodologies are inconvenient, costly and time consuming.

Menstrual cups have previously been used as feminine hygiene products for the purpose of collecting the menstrual fluid during menses. The menstrual cup is usually made of medical grade silicone, shaped like a bell and is flexible. It is worn inside the vagina during menstruation to catch menstrual fluid (blood). The menstruating woman removes the menstrual cup from the vagina, and disposes the collected menstrual blood, for example, into a toilet or sink.

SUMMARY

In one aspect, a fluid collection device for the collection and analysis of vaginal discharge fluids is provided. The device includes a novel fluid collection receptacle having a fluid tight lid for menstrual blood and/or vaginal fluid collection. The lid serves to seal the menstrual blood so it can be transported to a remote location for analysis, or preserved or otherwise handled.

In one aspect, a vaginal fluid collection system includes (i) a menstrual cup, the cup having a receptacle extending from an open top end to a closed bottom end and a stem attached to the receptacle at the bottom end thereof, the receptacle having an inner wall and an outer wall; and (ii) a lid dimensioned to fit on the open top end of the receptacle, the lid having an upper surface and a lower surface, wherein the cap and the open top end of the receptacle are dimensioned and arranged to engage to form a fluid tight seal.

In one or more embodiments, the collection system includes complementary threaded grooves on the lid and the top open end of the cup.

In one or more embodiments, the collection system includes depressions or slots located on the top open end of the cup and protrusions located on a circumference of the lid, wherein the protrusions are capable of engagement with the depressions.

In one or more embodiments, the lid and the open top end of the receptacle form a ball and socket mechanism.

In one or more embodiments, the collection system includes the sealing mechanism forming a snap-fit mechanism.

In one or more embodiments, the collection system includes the lid having an adhesive-backed sheet positionable to form an adhesive seal with the menstrual cup.

In any preceding embodiments, the collection system further includes an additive.

In one or more embodiments, the additive is an anticoagulant, preservative or antibiotic or other chemicals which may be used for the diagnostic assay or to lyse cells.

In one or more embodiments, the additive coats the inner wall of the cup and/or the lower surface of the lid.

In one or more embodiments, the additive is a fluid or solid housed within the cup.

In one or more embodiments, the collection system further includes a container housing the additive separate from the menstrual cup.

In any preceding embodiment, the collection system further includes a collection tube for storage of a vaginal fluid.

In one or more embodiments, the collection tube houses an additive.

In one or more embodiments, the additive is an anticoagulant, preservative and/or antibiotic or other chemicals for preservation of vaginal fluid or useful in the diagnostic chemical processes.

In one or more embodiments, the additive coats the inner wall of the collection tube.

In one or more embodiments, the additive is a fluid or solid housed within the collection tube.

In any preceding embodiment, the menstrual cup and/or the lid includes a computer readable identifier, RFID or any other kind of ID.

In any preceding embodiment, the collection system further includes packaging for use in shipping the sealed menstrual cup or the collection tube.

In aspect, a vaginal fluid collection system includes a fluid pervious top face sheet; a fluid impervious backing sheet; an absorbent pad disposed between the face sheet and backing sheet; and a fluid collection test strip having a grippable portion extending from an edge of the strip, the fluid collection test strip disposed in fluidic contact with the absorbent pad; wherein at least one of the backing sheet or the top face sheet comprises an opening sized to allow the removal and/or insertion of the fluids collection test strip from the fluid collection system.

In one or more embodiments, the grippable portion is disposed in the top face opening or the grippable portion is disposed in the backing sheet opening.

In any preceding embodiment, the fluid collection test strip is disposed between the top face sheet and the absorbent pad.

In any preceding embodiment, the fluid collection test strip is disposed in a recess defined in the absorbent pad.

In any preceding embodiment, the fluid collection test strip is disposed in a pocket located on the absorbent pad.

In any preceding embodiment, the pocket is made up of the top face sheet selectively adhered and non-adhered adhered to the absorbent pad to define the pocket.

In any preceding embodiment, the pocket opening is sized to allow the removal and/or insertion of the fluids collection test strip.

In any preceding embodiment, the fluids collection test strip includes a fluid absorbing layer disposed between upper and lower protective layers, the upper and lower protective layers having at least one opening, the at least one opening positioned to provide fluidic contact with the absorbent pad.

In any preceding embodiment, the fluids collection system further includes a fluid impervious layer disposed between the upper protective layer and the fluid absorbing layer, the fluid impervious layer having at least one opening to allow fluid flow to the fluid adsorbing layer.

In any preceding embodiment, the upper and lower protective layers and/or the fluid impervious layer, when present, includes a plurality of openings.

In any preceding embodiment, the fluid adsorbing layer includes a plurality of fluid adsorbing zones.

In any preceding embodiment, the plurality of fluid adsorbing zones are fluidically isolated from one another and in fluidic communication with different openings in the upper and lower protective layers.

In any preceding embodiment, the fluid adsorbing layer includes at least one whole blood test strip.

In any preceding embodiment, the fluid adsorbing layer includes at least one plasma-separating test strip.

In any preceding embodiment, the fluids collection test strip is coated and/or selected to have a pore size suitable to filter blood cells.

In any preceding embodiment, the fluid adsorbing layer includes at least one plasma-separating test strip and at least one whole blood test strip.

In any preceding embodiment, the plurality of test strips are in the same layer.

In any preceding embodiment, the fluids collection test strip includes a non-adsorbent sheet having at least one fluid adsorbent region in fluidic communication with the adsorbent pad.

In any preceding embodiment, the fluids collection test strip includes a color indicator selected to provide a visual indication of the presence of a biomarker in a vaginal fluid.

In any preceding embodiment, the color indicator is readable using a mobile device or other electronic reader.

In any preceding embodiment, the fluids collection test strip includes a computer readable identifier, RFID or other kind of ID.

In any preceding embodiment, the collection system further includes packaging for use in shipping the fluids collection test strip or component thereof.

In another aspect, a vaginal fluids collection test strip includes a fluid absorbing layer disposed between upper and lower protective layers, the upper and lower protective layers comprising at least one opening, said at least one opening positioned to provide fluidic communication to the fluid absorbing layer and the fluid absorbing layer comprising a plasma-separating test strip; a fluid impervious layer disposed between the upper protective layer and the fluid absorbing layer, the fluid impervious layer comprising a first opening to allow fluid flow to the fluid adsorbing layer and a second opening defining a window for viewing separated plasma.

In any preceding embodiment, the upper and lower protective layers include a plurality of openings.

In any preceding embodiment, the fluid adsorbing layer includes a plurality of fluid adsorbing zones.

In any preceding embodiment, the plurality of fluid adsorbing zones are fluidically isolated from one another and in fluidic communication with different openings in the upper and lower protective layers.

In any preceding embodiment, the fluid adsorbing layer includes at least one plasma-separating test strip and at least one whole blood test strip.

In any preceding embodiment, the fluid adsorbing layer includes two plasma-separating test strips.

In any preceding embodiment, the fluids collection test strip includes a color indicator selected to provide a visual indication of the presence of a biomarker in a vaginal fluid.

In any preceding embodiment, the fluids collection test strip includes a computer readable identifier, RFID or other kind of ID.

In another aspect, a vaginal fluid collection system is provided having an absorbent layer having a separable absorbent portion, the separable absorbent portion in fluidic contact with the absorbent layer, wherein the absorbent layer is integrated into a tampon, panty liner or menstrual pad.

In any preceding embodiment, the absorbent layer includes an opening, wherein the opening provides access to the separable absorbent portion and wherein the opening is sized to permit passage of the separable absorbent portion.

In any preceding embodiment, the separable absorbent portion is attached to a string accessible external to the tampon, panty liner or menstrual pad.

In any preceding embodiment, the vaginal fluid collection system further comprising packaging for use in shipping the separable absorbent portion.

In another aspect, a website, an app or another digital service and display is provided, which stores vaginal fluid analysis information obtained in the method according to any preceding embodiment and displays the information to the user or a medical professional.

In still another aspect, a method of analyzing vaginal fluid is provided and includes collecting vaginal fluid in a vaginal fluid collecting system according to any of the embodiments described herein; and analyzing the collected vaginal fluid.

In any preceding embodiment, the method further includes transporting the collected vaginal fluid to a location for analysis.

In any preceding embodiment, the method further includes receiving analytical data relating to the analysis of the vaginal fluid sample.

In any preceding embodiment, the collection device is a fluid collection test strip strip and the analysis includes screening for presence of human fluids collection test strip.

In any preceding embodiment, the collection device is a a fluid collection test strip strip and the analysis includes detection or screening of any other health related biomarker including but not limited other viruses, bacteria and fungi.

In another aspect, a urine collection system is provided and includes an absorbent pad having a top face sheet; a fluid impervious backing sheet; an absorbent pad disposed between the face sheet and backing sheet; and a dried urine spot test sheet having a grippable tab extending from an edge of the sheet, the dried urine spot test sheet disposed between and in fluidic contact with the absorbent pad and the backing sheet;

wherein the backing sheet comprises an opening sized to allow the passage of the dried urine spot test strip and wherein the grippable member is disposed in the backing sheet opening.

In one or more embodiments, the absorbent pad is integrated into a diaper.

In one or more embodiments, the absorbent pad is integrated into a feminine hygiene product.

The menstrual blood diagnostic described herein provides a novel device (menstrual cup+lid) that allows the home collection of a blood sample; the device allows the sample to stay sterile inside the cup, without the need of pouring it into another collection tube. The process of taking a used menstrual pad and tampon and putting it into a small bag, before sending the material to a remote location for analysis, is also not described in prior art.

BRIEF DESCRIPTION OF THE DRAWINGS

FIG. 1 is an exploded version of a menstrual cup with a lid according to one or more embodiments.

FIGS. 2A-D illustrate a menstrual cup but with different lid embodiments.

FIG. 3 illustrates a concept of menstrual blood collection using a menstrual cup and blood collection tubes according to one or more embodiments.

FIGS. 5A and 5B illustrates the dried blood testing card and its cover according to one or more embodiments.

FIG. 5C illustrates a DBS/DUS-card, which detects and/or measures health markers using colorimetric detection methods according to one or more embodiments.

FIG. 5D illustrates the same card but where the results are given and interpreted using a mobile device according to one or more embodiments.

FIGS. 8A-8E illustrates the blood collection strip according to one or more embodiments, which could allow for the plasma separation.

FIGS. 9A-9D is another embodiment of the blood collection strip according to one or more embodiments.

FIGS. 10A-10D is another embodiment of the blood collection strip according to one or more embodiments.

FIG. 16A-16B illustrates the operation of the fluid collection test strip in FIG. 10 according to one or more embodiments.

DETAILED DESCRIPTION

Figure 2D:
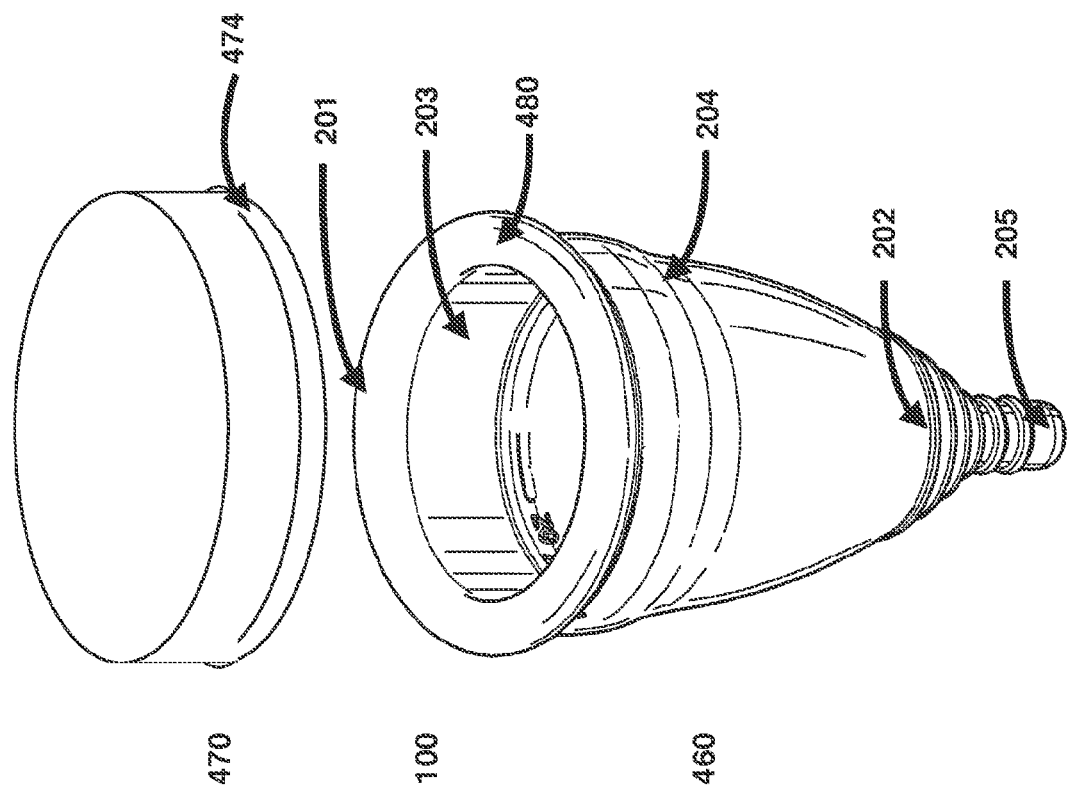

A fluid collection system is described for the collection, storage, transport and analysis of vaginal fluids. As used herein, 'vaginal fluid' refers to any fluid that can be collected from the vaginal cavity. Exemplary fluids include biological fluid secreted from the vagina throughout the various stages of the menstrual cycle, including menstrual blood. It can also include fluids that can be collected from the vagina. A fluid collection device is also described for the collection and analysis of urine. In other embodiments, urine may be collected with vaginal fluids, such as for example, when traces of urine are collected from around the vagina.

Reference is first made to FIG. 1 to describe an embodiment of a menstrual fluid collection system in accordance with the invention indicated generally by the numeral 100. The menstrual fluid collection system includes a fluid receptacle 200 and sealing cap 300. The receptacle 200 is adapted to be flexible and resilient. The general structure of the fluid receptacle 200 can be adapted from menstrual cups used for the collection of menstrual fluid during menstruation. The receptacle extend from an open top end 201 to a closed bottom end 202 and an optional stem 203 attached to the receptacle at the bottom end thereof, for use in insertion and removal of the cup or fluid receptacle. The receptacle includes a wall having an inner wall surface 203 defining a cavity adapted for collecting fluid and an opposed outer wall surface 204. The open top end has a predetermined diameter, and includes a rim 210 adapted to provide resilient outward holding force sufficient for holding the receptacle in position within a woman's vaginal canal during use. Upper rim 210 acts as a stabilizer once the cup is in use. The system also includes a lid 300 that engages with upper rim 210 of the cup to create a fluid-tight seal to store collected fluid and permit transport. The upper rim also includes a sealing feature that can be used as part of a closing mechanism with a lid 300. In one or more embodiments, the upper rim 210 is functionalized with grooves 220, e.g., threaded groove, to facilitate fluid-tight sealing. Lid 300 contains complementary threaded grooves (not shown) that engage with those of the fluid receptacle to form a fluid-tight seal.

The inner surface 203 of the fluid receptacle can be pre-coated with a substance that preserves the fluid sample or assists in its preparation for analysis. For example, the inner surface can be coated with, e.g., anticoagulants, preservatives, an antibiotic or other agent to prevent the growth of bacteria or other microorganisms or other chemicals which may be used for the diagnostic assay or to lyse cells, selected for the purpose of lengthening the durability and preserving the menstrual blood for transportation to a remote location for analysis. Exemplary additives include EDTA, sodium citrate, clot activators, such as heparin, lithium heparin, sodium heparin, ThinPrep, thrombin-based clot activators, $K_2EDTA$, fluoride, oxalate or sodium polyanethol sulfonate, collagenase, PBS or other chemical preservatives or stabilizers. The substance can be a coating, liquid, powder or a gel coating all or a portion of the inner surface of the wall 203 or an inner surface of lid 300 that is capable of contact with a fluid contained within the receptacle. In other embodiments, an additive may also be a powder or liquid that is added to the cup, e.g., located at the bottom of the cup 202, for or after fluid collection. The outer wall surface 204 may also include a coating such as a lubricant or similar materials, which eases the insertion of the fluid receptacle. The fluid receptacle or the lid (or both) can have a barcode and an ID code to uniquely identify the sample.

FIG. 1 further illustrates the mechanism of sealing a menstrual blood collection device 100, which consists of screwing threaded lid 300 onto rim 210 of a menstrual cup 200 having complementary threads 220. On the upper part of the menstrual-cup 201, the upper rim 210 is shaped with external threads 220. The lid 300 has internal threads (not shown) so that it can be screwed on to the upper rim 210 of the cup. In other embodiments, the thread can he reversed, so that the inner surface of the upper rim 210 is threaded on the outer circumference of the lid is threaded. The engaged threads seal in the menstrual blood so it can be transported to a remote location for analysis.

The menstrual fluid collection system in accordance with the invention can include any lid and fluid sealing mechanism that provides a fluid-tight and optionally gas-tight fit. Exemplary sealing methods are illustrated in FIGS. 2A-2D. The cap can include an optional gasket (not shown) to increase water and gas impermeability.

In FIG. 2A, a fluid receptacle 400 is illustrated with a push lid 405. Small depressions or slots 404 are located on an upper portion of the fluid receptacle below and in proximity to upper rim 410. The depressions 404 are shaped to engage with protrusions, hooks or clips 402 located on a lower circumference of lid 405, and serve as a closing mechanism for the menstrual fluid collection system. The depressions can be in the shape of holes or a slot. When the lid is pushed on to the cup, the hooks slide over upper rim 410 and engage with slots 404 to seal the menstrual sample collected inside the cup. The small holes will also prevent vacuum when the menstrual cup is inside the vagina. The hooks can be evenly spaced around the perimeter of the menstrual cup opening for better stability. The cap can include an optional gasket (not shown) that engages with the upper surface 201 of the fluid receptacle to create a fluid-tight seal.

In another embodiment, the seal is formed between the cap and an enlarged rim of the menstrual fluid receptacle. In one embodiment, FIG. 2B illustrates a menstrual fluid receptacle 420 and a lid 430 with a round enlarged rim 440. Fluid receptacle 420 includes an upper rim 425 that is slightly thicker, e.g., of larger diameter, than the rest of the cup. When the lid 430 is pressed on top of the cup, the rim 440 of the lid engages with upper rim 425 to seal the lid to the cup. Lid 430 can be pushed below the upper rim 425 of the menstrual cup 420 to complete the seal. Lid rim 440 is pliant so that is can be pushed on to cup 420 and over upper rim 425 to engaged with the lower edge 428 of upper rim 425. Once the lid is pushed down on top of the cup, it will effectively seal the sample collected inside, e.g., a snap-fit mechanism. FIG. 2C includes a similar sealing mechanism, except the closing mechanism in FIG. 2C does not include a rim 440. In FIG. 2C, the lid 430 slides over the upper top of rim 425 of the fluid receptacle. The cup can be coated with an adhesive on the inside on the cup which will then seal the lid to the cup.

In another embodiment, the seal between the cap and menstrual cup is a "ball and socket" design, in which a ball-shaped or convex curved surface of one of the elements fits into a cup-like depression or concave curved surface of the other. In one or more embodiments, the upper rim of the receptacle has the curved surface and an inner surface of the lid provides the cup-like depression. In FIG. 2D, a fluid receptacle 460 is illustrated with a lid 470, in which the upper rim 480 of the cup has a rounded and curved form, so when the lid 470 is pushed on top of the rim 480, an inner surface of the lid rim 474 seals around the inside and outside of the surface area, making a tight and enclosed space for the collected menstrual sample. The closing mechanism between the menstrual cup 460 and the lid 470 functions like a ball and socket mechanism.

Figure 2E:
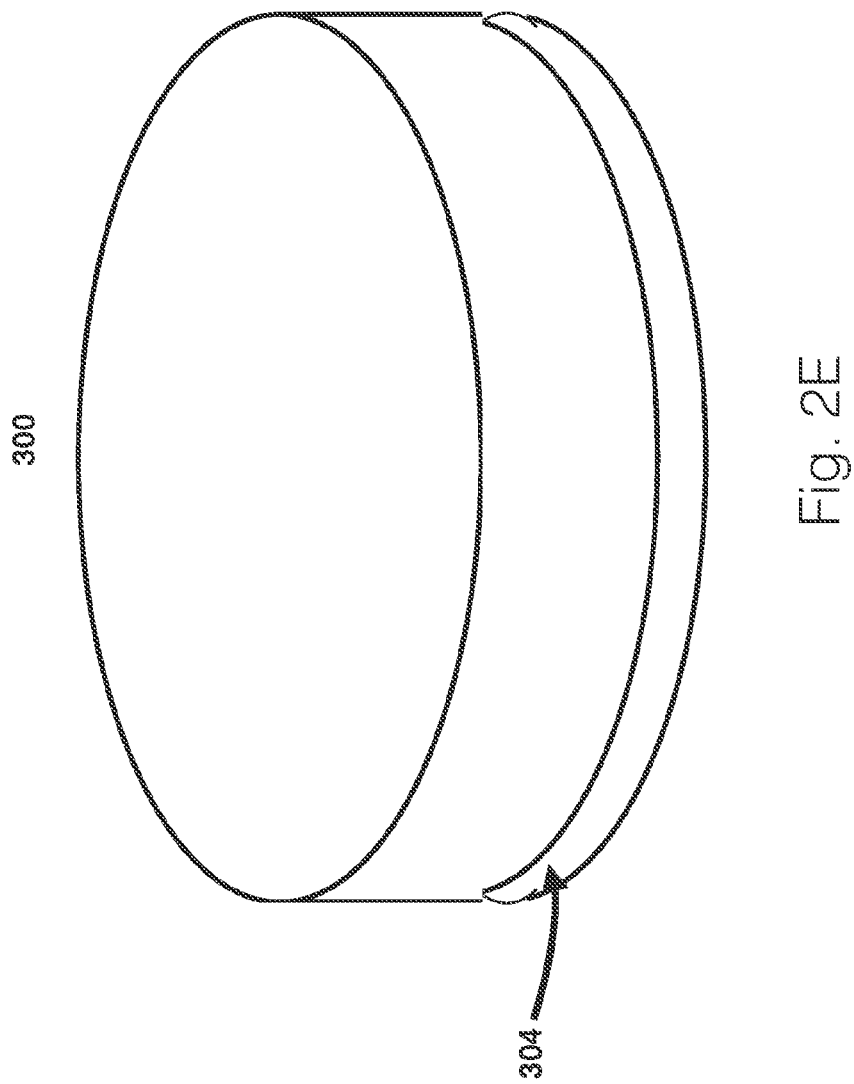
FIG. 2E illustrates only the menstrual cup lid, which is designed to fit any menstrual cup including the ones already on the market.

In other embodiments, the cap can be adapted to engage with commercially available menstrual cups, which can be used as fluid receptacles according to one or more embodiments. FIG. 2E illustrates a universal lid designed to work with any cup found in prior art of menstrual cups, e.g. Chambers US20080077097 A1. For example, the lid can include an adhesive on the inside which will form a liquid-tight seal with any cup. In other embodiments, the lid can include an adhesive-backed sheet. The sheet can be peeled off to expose the adhesive that is then used to seal the lid to the cup.

In one or more embodiments, the flexible fluid collection system is made of elastomeric material. In one or more embodiments, the cup is molded and can be, for example, formed in an injection mold. In other embodiments, the elastomeric material is a latex rubber or an organosilicon oxide polymer, i.e., a silicone rubber. Silicone rubber is used preferred because it rarely (if ever) causes skin irritation, and it has the necessary resiliency and durability. The silicone rubber is preferably a medical grade which is already FDA approved.

In use, the woman folds the cup lengthwise and inserts the cup into the vagina, top end first. Once inserted, the top end returns to its usual size and is nested on the cervix. The cup is preferably positioned relatively low in the vagina so that it may be easier to remove, and also to prevent leakage. When the woman wants to remove the cup, she grasps the stem and pulls the cup out. Once the cup is taken out of the vagina, the lid is secured to the cup, to seal and close the menstrual fluid sample inside the cup. In some embodiments, the menstrual cup is coated with or contains all the additives needed for the preservation and/or stabilization of the sample before and during transport. In other embodiments, stabilizing and/or preserving components are provided separately and are added to the collected menstrual blood after collection and before storage and transport. In one or more embodiments, the collected fluid is transported to a lab for diagnostic testing. The fluid receptacle or the lid can have a barcode and an ID code to uniquely identify the sample. Both the user and the analytical laboratory can scan the ID code, e.g., with a smartphone or other scanner, or manually enter to register the sample and/or associate the sample with a user profile. Results from the laboratory can be sent to the user with the same barcode, for example, by mail, phone or in a mobile application or website.

In other embodiments, the menstrual blood is transferred to a collection tube before transporting to a remote location, as is illustrated in FIG. 3. In one or more embodiments, a fluid collection receptacle 510 is used as a collection device of vaginal fluid 520. After collection, the vaginal fluid content 520 is transferred to a blood collection tube 500. In one or more embodiments, the collection tube is sterile. In one or more embodiments, the collection tubes contain an antibiotic or other agent to prevent the growth of bacteria or other microorganisms. The inside of the collection tube may pre-coated with a substance of e.g. anticoagulants, EDTA, sodium citrate, heparin, lithium heparin, sodium heparin, potassium salt, $K_2$EDTA, ThinPrep fluoride, oxalate or sodium polyanethol sulfonate. Once the menstrual fluid is in the tube, the coating is used to lengthen the durability and lastingness of the collected menstrual blood, before it is mailed to a remote location for fluid analysis as shown in FIG. 8A. The menstrual collection tubes can have a barcode and an ID code which the user and lab can scan with a smartphone or manually enter to register the sample and/or associate the sample with a user profile. Results from the lab can be send to the user with the same barcode, for example, by mail, phone or in a mobile application or website.

To keep the liquid blood sample viable for testing, a process for cold chain goods can be implemented. Depending on the specific testing, transit containers, packing materials and procedures are validated, to ensure the component surface temperature can be maintained between 2-10 Celsius during transportation. As far as practicable, transit containers should be equilibrated to their storage temperature prior to filling with components. If melting ice is used to keep the blood specimen cold, it should not come into direct contact with the components. Dead air space in packaging containers should be minimized, and transport time normally should not exceed 12 hours. In one or more embodiments, the sample is transported using a blood shipment kit. The blood shipment kit can include a cooling box (e.g. foam box) or other thermally insulating outer container, a secondary receptacle with adsorbent (e.g., towel) and gel packs for cooling.

In one or more embodiments, a vaginal fluid collection kit includes a vaginal fluid collect receptacle with fluid tight lid. The kit can optionally also include one or more of the following: (i) packets of additive (with instructions to add the additive into the vaginal fluid collect receptacle), (ii) collection tubes (with instructions to transfer the collected vaginal fluid into the tubes before transport), and (iii) a blood shipment kit (with instructions for the preparation and shipping of the collected vaginal fluid sample). In one or more embodiments, the kit includes a return package that would allow the sample to be packed into ice or other cold storage shipping process.

In another aspect, the menstrual blood can be collected and transported as a dried sample on a stabilizing substrate. The dried sample may be more stable, weigh less and provide a ready format for testing on receipt at a remote testing site. In one or more embodiments, menstrual fluid collection is accomplished using a dried blood spot (DBS) fluid collection pad, alternately referred to herein as a fluid collection test strip (FCTS). The fluid collection test strip uses an adsorbent layer, such as paper or cellulose, as the stabilizing substrate. In certain embodiments, the stabilizing substrate is used to collect and store blood. In some embodiments, as is described in greater detail herein, the pore size and chemical treatment of the layer does not distinguish or filter the various blood components and the dried blood spot will contain "whole blood," herein referred to as a "whole blood test strip." In other embodiments, as is described in greater detail below, the pore size and chemical treatment of the layer is selected to filter the various blood components. For example, pore size can be selected to allow flow of the blood plasma, while retaining the larger red and white blood cells. The fluid collection test strip will contain a region of red and white cells and a region containing blood plasma, herein referred to as a "plasma-separating test strip." Where not specified, the fluid collection test strip can contain either whole blood test strip or plasma-separating test strip or both. Furthermore the terms "dried blood spot" sheet, DBS-sheet, fluid collection test strip, and FCTS are used interchangeable, unless otherwise specified.

Figure 4B:
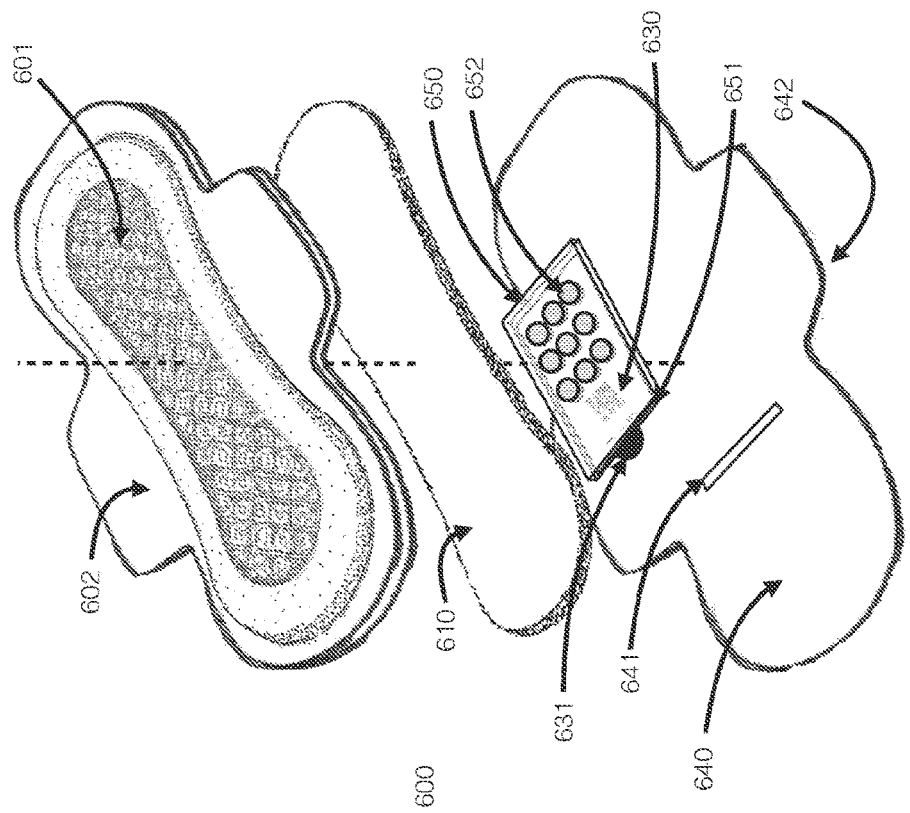
FIGS. 4A and 4B illustrate two embodiments of a dried blood spot testing menstrual pad according to one or more embodiments.
Figure 4A:
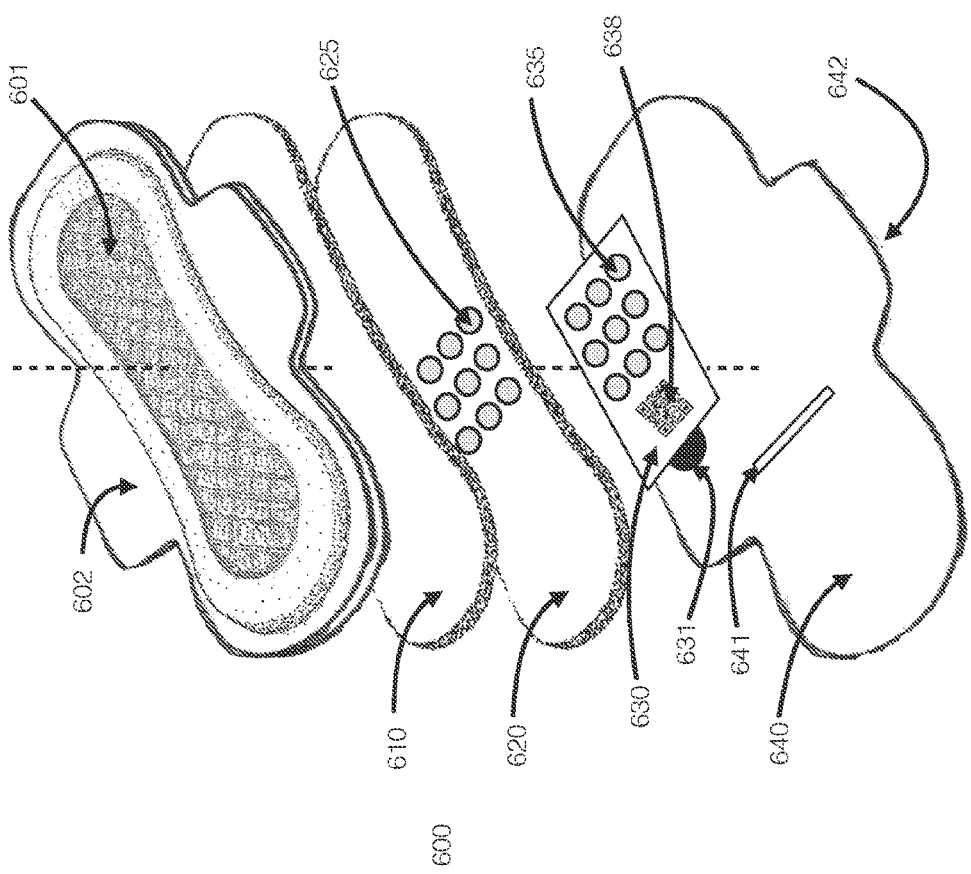

In one or more embodiments, the fluid collection system can be adapted using the sorbent materials and attachment features of conventional menstrual pads. FIGS. 4A and 4B illustrate two embodiments of a dried blood spot menstrual pad (DBS-pad) 600. The DBS-pad 600 consists of a fluid collection pad and a dried blood spot card 630. The adsorbent pad is made of cellulosic or synthetic absorbent material and can be prepared without scents, antimicrobial agents or other drugs/chemicals. The indication of use is for absorption and analysis of menstrual or other vaginal discharge. The device is designed to acquire and hold vaginal fluids, menstrual fluids or light urine.

FIG. 4A is a DBS-pad 600, which has an upper permeable top-sheet layer 601 which allows fluid to pass through to the core layer 610. The DBS-pad 600 may or may not have wings 602 to increase the stability of the pad in the user's underwear. The layer below the upper permeable layer is an absorbent core 610 which acquires and stores fluid. The absorbent core 610 is disposed over an optional impermeable cover layer 620 which however has one or more inlets 625 to allow fluid to travel through to a dried blood spot (DBS) card 630. The DBS-card absorbs a certain amount of menstrual or vaginal discharge. The absorbent pad and the dried blood spot sheet are in fluidic contact with each other through inlets 625 of impermeable cover layer 620. Fluidic contact or fluidic communication as used herein means that fluid flow through the layers is possible when a fluid is present. The impermeable back sheet 640 prevents fluid transfer. The DBS cardboard 630 is secured to the back sheet 640 using tab 631 which can be positioned to be insertable through a slit or opening 641 in the impermeable back sheet 640 of the pad. On the external backside of the pad is an attachment adhesive 642. The tab 631 will be visible on the external backside of the pad once the attachment adhesive 642, which holds the pad in place, is removed.

Another embodiment of a DBS testing menstrual pad is shown in FIG. 4B. The cover layer 620 shown in FIG. 4A is absent in FIG. 4B and instead a cover sheet 650 around the DBS-card 630 is provided. The cover sheet can be of a flexible but impermeable material including but not limited to plastics, e.g., ABS (acrylonitrile butadiene styrene) Acrylic (also known as Plexiglas, Lucite, PMMA), thin metals: Stainless steel (up to 0.060") Spring steel (up to 0.060"), foam: Depron foam—often used for RC planes, EPM, Cloths (impregnated leather, suede, felt, hemp, cotton) or magnetic sheets. Cover sheet 650 includes one or more inlets 652 to allow fluid to travel through to a dried blood spot (DBS) card 630. The absorbent pad and the dried blood spot sheet are in fluidic contact with each other through inlets 652 of cover sheet 650. The cover 650 can be secured to back sheet 640, for example, using an adhesive. For a better illustration of the cover with DBS testing cardboard see FIG. 5B. In the one end of the cover there is an opening 651. The tab 631 sticks out of the opening 651 and passes through slip or opening 641 in the impermeable back sheet 640. The tab 631 will he apparent on the external backside of the pad once the attachment adhesive 642, which holds the pad in place, is removed.

In another embodiment, the opening 651 in the back of the cover is closed and instead the slip 631 comes out of an opening beneath the cover where opening in the back sheet of the menstrual pad 641 will also be located. In this case vaginal fluid does not leak.

In use, a protective sheet that covers the adhesive 642 is peeled away and the pad 600 is secured to the undergarment of the user in much the same way as a menstrual pad. The user places the DBS-pad in her underwear. The blood runs through the layers of the pad, and is aggregated in the bottom of the pad where a small cardboard or paper sheet absorbs the blood through one or more inlets. After the DBS-pad has been in place for a time sufficient for vaginal fluid to be absorbed into the dried blood spot plate, the pad is removed. After usage, the pad is removed and tab 631 on the backside of the pad is pulled and the DBS testing card is pulled out from the opening in the bottom layer 641 of the pad. The cover 650 remains inside the pad. The pad can be disposed of, while the DBS cardboard can be used for health analysis.

Figure 5A:
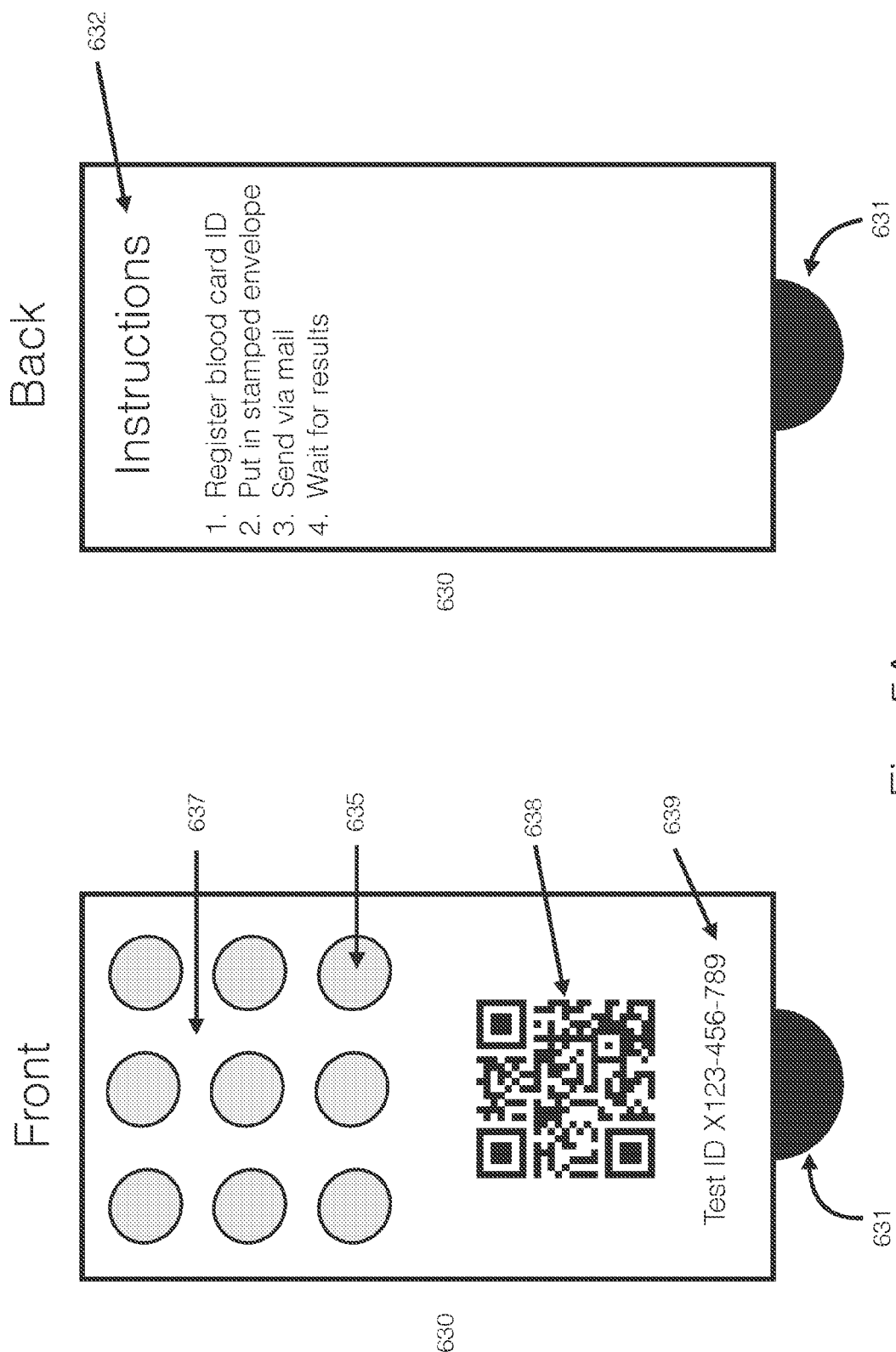

FIG. 5A is a front and back view of an exemplary DBS testing card 630. The cardboard has absorbent areas 635, which absorb and filters menstrual and vaginal fluid, that are defined by non-absorbent regions 637. Absorbent areas 635 are the areas which will absorb blood, while the rest of the sheet does not. The sheet may be of different format and sizes as is described herein below. The absorbent regions may be circular as shown in this illustration or any other format and may consist of multiple layers of membranes and filters. There may be multiple areas as illustrated here or one larger area of absorption. The DBS testing cardboard has a barcode 638 and an ID code 639 which the user and laboratory can scan with a smartphone or other scanner or manually enter to register the DBS testing cardboard 630 with the user's profile. Results from the laboratory will he sent to the user with the same barcode and shown in a mobile application or website. On the backside of the DBS testing cardboard 630 are the user instructions 632. FIG. 5B shows the same DBS-card inside a protective cover 650, which has openings 652 that ensures blood can flow into the pad and only contacts the areas of absorption 635. The DBS-card is removable from the protective cover 650 by pulling on tab 631.

FIG. 7 is another embodiment of a dried blood spot testing menstrual pad and illustrates a menstrual pad with a blood collection device strip which can easily be removed from the pad, according to one or more embodiments This strip allows for plasma separation.

Figures 7A, 7B, 7C, 7D:
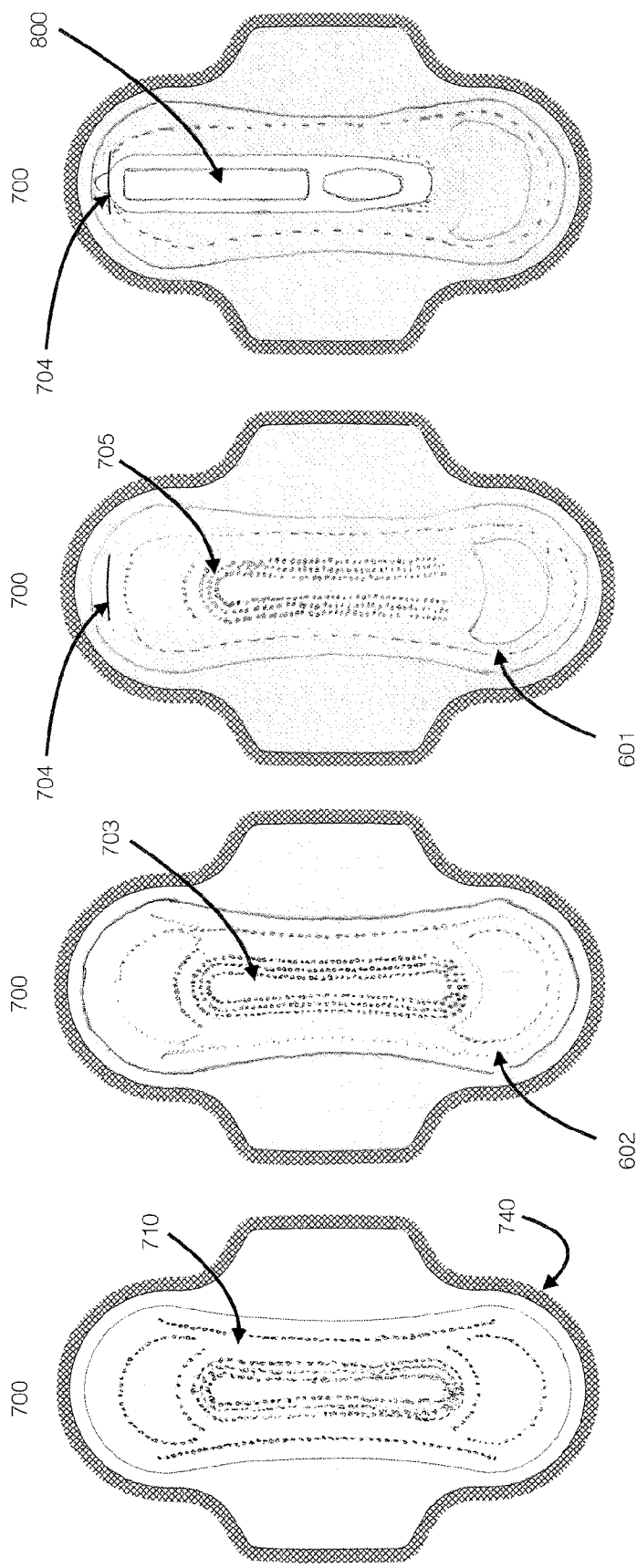
FIGS. 7A-7D is another embodiment of a dried blood spot testing menstrual pad and illustrates a menstrual pad with a fluid collection test strip which can easily be removed from the pad, according to one or more embodiments; this strip can allow for whole blood separation or plasma separation.

In one or more embodiments, the fluids collection test strip is reversibly insertable into an adsorbent fluid collection pad. The fluids collection test strip can be inserted into the pad shortly prior to use or can be obtained in an assembled format. The strip may also be inserted during manufacturing. In one or more embodiments, the fluid collection test strip can easily be removed from the adsorbent pad. The adsorbent pad 700 has an impermeable back sheet 740, an absorbent core 710, which is illustrated in FIG. 7A. The fluids collection test strip 800 can be secured on the adsorbent core 710 using a liquid permeable top layer 701 that is adhered to the absorbent core 710, for example using adhesive 702, and includes a recess or pocket 705 for the test strip. A slot 704 allows for easy insertion and/or removal of the fluids collection test strip. In FIG. 7B, adhesive or glue 702 is dispersed on top of the absorbent core illustrated as the dark grey areas. A glue-free area 703 serves as the base for pocket 705 in which the fluid collection test strip can placed. FIG. 7C shows the placement of permeable top sheet 701 on top of the absorbent core 710, where the glue 702 keeps it in place. Additionally, the top sheet 701 has an open slot 704 which allows the insertion and removal of the fluid collection strip 800, as is shown in FIG. 7D.

An exemplary fluids collection strip 800 is shown in FIGS. 8A-8D. The strip has an upper protective cover 801 illustrated in FIG. 8A, which is secured, e.g., by adhesives applied to the top frame 810. The protective cover 801 can be removed after the strip 800 is removed from the used pad 700. The protective cover 801 can be made of any material permeable for air, but impermeable to liquid. The upper protective cover has an inlet 802 which allows vaginal fluid and menstrual blood to flow into the strip and be absorbed by an absorbent material 820. In exemplary embodiments, the absorbent material is paper. The absorbent paper material 820 can be of any kind of dried blood spot paper and can be treated or untreated to stabilize certain pathogens, proteins, DNA, RNA or other biomarkers of interest. The paper can be coated and/or selected to have a pore size suitable to filter blood cells, allowing red blood cells and plasma to be separated. Beneath the protective layer 801 is a top frame 810 illustrated in FIG. 8B, which can be made of any material impermeable to air and liquid. This layer also has an inlet 812 which allows vaginal fluid and menstrual blood to flow into the strip and be absorbed by absorbent material 820. Further, the top frame also has an opening 811 which functions as a plasma collection window. Beneath the top frame of the strip is the absorbent paper material illustrated in FIG. 8C, which absorbs and separates menstrual blood into whole blood and plasma. Whole blood is collected in the inlet area of the strip, while clear plasma fluid will appear in the plasma window area of the strip. The inlets in the protective cover 802 and the top frame of the strip 812 allows menstrual blood and vaginal fluid to be absorbed in the confined area of the absorbent paper material below inlets 802 and 812, but not in the plasma window area 811. Fluid adsorbed in this area flows laterally from the inlet area of the absorbent paper material to the plasma window area. In this process the material separates the red and white blood cells from the plasma. Consequently, the inlet area will contain whole blood while the plasma window will contain clear menstrual blood plasma. FIG. 8D shows the bottom frame of the strip 830, which is made of a similar material to the upper frame 810. The bottom frame 830 also has an outlet 831 which allows excessive fluid to pass through, which prevents it from travelling from the inlet to the plasma window. Excessive fluid is absorbed by the absorbent core 810 of the menstrual pad. More layers, for example, additional frame and absorbent material layers are contemplated.

FIG. 8E shows an exploded view of the blood absorbing strip 800. The protective cover 801 has adhesive on the back side 804 which sticks to the top frame of the strip 810 but due to the inlets and the plasma window inlet it will not adhere to the absorbent paper material 820. On the backside of the top frame of the strip is also adhesive 814 which adheres to the bottom frame 830, but again it does not stick to the absorbent paper material 820.

In other embodiments, the fluids collection test strip can include a plurality of inlets. In one or more embodiments, the one or more inlets are in fluid communication with a plurality of adsorbent material zones on the absorbent material layer. In one or more embodiments, the adsorbent material zones are fluidically isolated from one another, that is, the two fluid flows do not comingle. FIGS. 9A-9D illustrate the four layers of an embodiment of the fluid collection strip 900 which has two inlets 902 in the protective cover and the top frame of the strip 912. More layers, for example, additional frame and absorbent material layers are contemplated. In this embodiment, however the absorbent paper material is split into two zones 920 and 921. This makes it possible to treat the different areas of the paper absorbent material with different reagents to allow for more analysis from one strip. In this embodiment 921 does not separate the menstrual blood into whole blood and plasma. This separation only happens in 920, where the absorbent paper material 920 can be of any kind of dried blood spot paper and can be treated or untreated to stabilize certain pathogens, proteins, DNA, RNA or other biomarkers of interest. The paper can be coated and/or selected to have a pore size suitable to filter blood cells, allowing red blood cells and plasma to be separated. The bottom frame consequentially also has two inlets 931.

In other embodiments, the fluids collection test strip provides for separation of menstrual blood into whole blood and plasma in a plurality of zones. In FIGS. 10A-10D, another embodiment of the strip 1000 is illustrated, in which the absorbent paper material layer includes a plurality of absorbent material zones. See, FIG. 10C. The zones are positioned with respect to the inlets 1002 and 1212 to provide plasma separation from both inlets. In this case 1020 and 1021 both does plasma separation which will be seen in the two plasma windows 1011 shown in FIG. 10B. The paper materials 1020 and 1021 can he of any kind of dried blood spot paper and can be treated or untreated to stabilize certain pathogens, proteins, DNA, RNA or other biomarkers of interest. The paper can be coated and/or selected to have a pore size suitable to filter blood cells, allowing red blood cells and plasma to be separated. In FIG. 10D the bottom frame 1030 of the strip 1000 is illustrated, again with two outlets 1031.

Figure 4C:
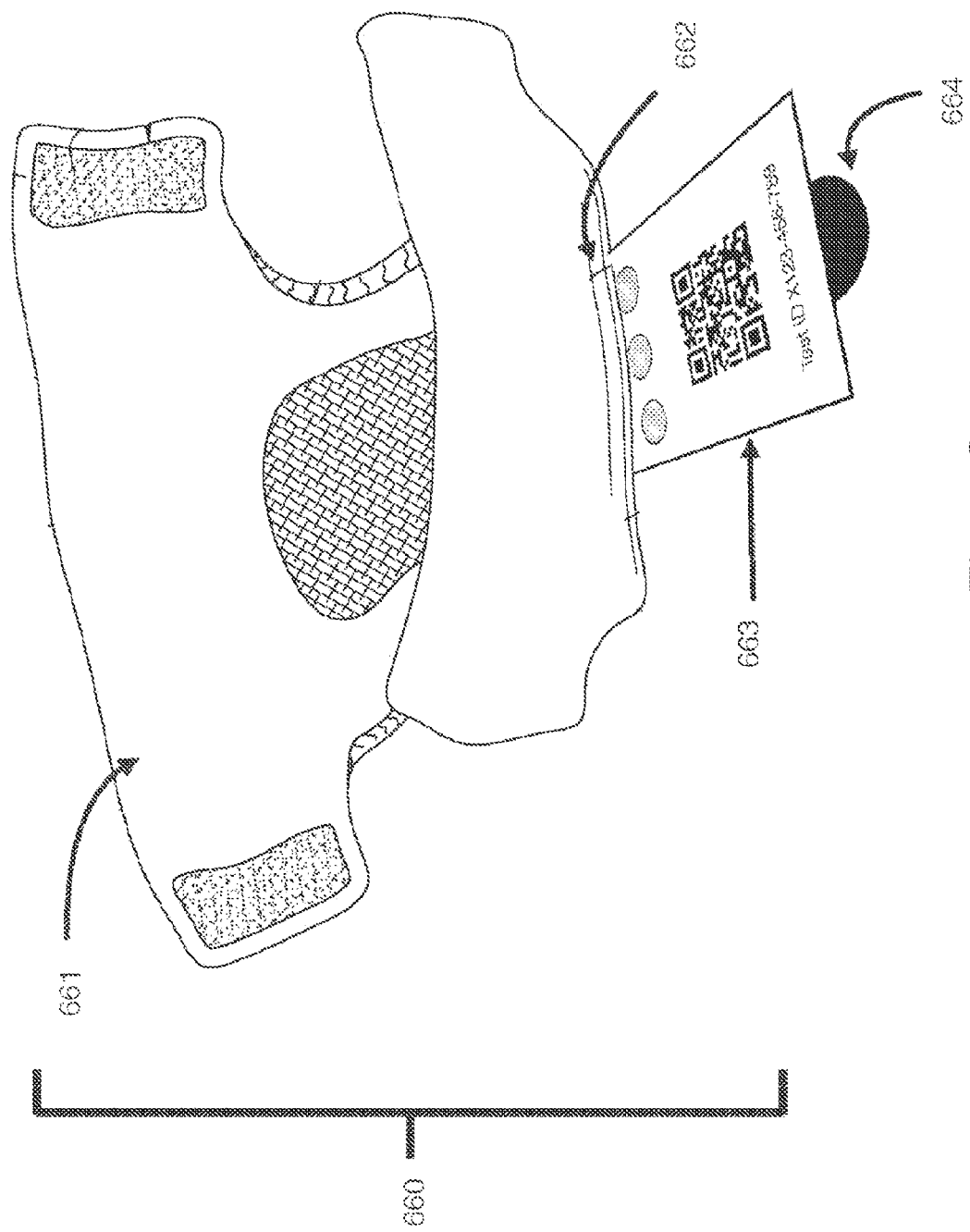
FIG. 4C illustrates the embodiment of a novel dried urine sport testing urine collection device, here illustrated as a diaper according to one or more embodiments.

The same concept can also be used in tampons and panty liners or for urine analysis using dried urine spot cards (DUS-cards) in e.g. diapers as shown in FIG. 4C. FIG. 4C illustrates a DUS-device 660, here as a diaper 661 but could be any urine collection device for both children and adults. The urine collection device has a DUS-card 663 with a tab 664 which can be pulled out of an opening 662 in the urine collection device and sent in for analysis in a remote location.

In one or more embodiments, the fluids collection test strip may be coated or be of different pore sizes to filtrate blood cells and may also be of multiple layers. A DUS-card can include the same features of fluid impermeable and fluid-sorbent regions as described for the DBS-card in FIG. 5A or the multilayer fluids collection test strip as shown in FIGS. 7-10.

In one or more embodiments, the fluids collection test strip can include an additive that is capable of diagnosing various health markers using colorimetric detection methods. In the embodiment, a color represents the presence or absence of a biomarker. The results could be interpreted by a mobile device or similar especially if the biomarker is quantifiable. The use of a colorimetric detection provides the additional flexibility on on-location diagnosis, and transport of the fluids collection test strip is not required for diagnosis. Biomarkers which could be analyzed includes pathogens such as bacteria or viruses such as the human papilloma virus, but also biomarkers such as Hemoglobin Alc, Lipids, Hormones, cancer markers and others.

The materials 820, 920, 921, 1020, 1021, 1100 can be made of materials which filters and separates whole blood into its various components. Any kind of cellulose material can be used. The materials may allow a high flow rate and high plasma yields, often used for both lateral and vertical flow amino assays. Media used in prior art can efficiently separate samples at a broad range of whole blood sample volumes. The plasma separating material can be made of e.g. glass borosilicate glass microfiber filter media containing unique acrylic binder systems but also many other variants are available and in development. Some materials may be treated with a coating technology which can improve the plasma seperation, while at the same time lowering red cell lysing from the sample area. The type of paper or plasma seperation material can vary in thickness and density, which influences the rate of adsorption and dispersion. One of the advantages of glass fiber material is that it does not soak up reagents, which leaves less non-specific analyte adsorption on the membrane. The specific glass fiber material chosen can be optimized for efficient separation of plasma from whole blood. On both cotton based and fiber glass materials, treatment can be added for DNA/RNA stabilization. The treatment can be added directly to the glass microfiber collection area. Commercially available methods can lyse cells exposing DNA/RNA, denature proteins and enzymes, and prevent microbial growth enhancing preservation for storage and analysis of nucleic acids. The cotton and fiberglass materials 820, 920, 921, 1020, 1021, 1100 can be produced by e.g. GE, IW Tremont or Perkin Elmer Ahklstrom and other manufactures.

The DBS cardboard can be composed of non-cellulose or cellulose (filter paper) matrix of specific pore size and thickness. Various commercial DBS cards are available, namely Whatman 903 cards FTA DMPK type-A, B, C cards and FTA Elute cards (GE Healthcare, Piscataway, N.J., USA), as per the type of analytical requirements. Routinely, Whatman 903 cards are basically used in newborns screening, FTA DMPK type A, B, C cards are used in PK/TK studies and FTA Elute cards are intended mainly for collection and purification of DNA for downstream analysis. All types of DMPK cards are available in two forms: regular and indicating. Indicating cards are useful for colourless samples like urine, plasma, synovial fluid, and cerebrospinal fluid and will most likely not be applicable in this use case. DMPK type A and B cards are chemically treated with proprietary reagents that, on contact cause lysis of cells, denature proteins, inactivate enzymes, and prevent the growth of bacteria. These coated cards are prepared to cause lyses of both cellular and nuclear membranes to expose nucleic acids with good stability for storage and analysis. These DMPK cards also inhibit the enzymatic degradation of several analytes namely procaine and acetyl salicylic acid from esterases which are present in the blood. These enzymes are denatured and inactivated when blood is spotted on the card leading to enhanced analyte stability. DMPK-C and Ahlstrom 226 cards (ID Biological Systems, Greenville, S.C.) are not treated with any chemical; therefore, there are no impregnated chemicals to interfere with the analysis. Moreover, proteins will not be denatured thus DMPK-C and Ahlstrom 226 cards may be better choice for protein based biomolecules analysis.

US Food and Drug Administration (FDA) has approved three DBS cards, namely Ahlstrom 226-K062932, Whatman 903 and PerkinElmer 226 under 21 CFR 862.1675 as medical device for blood specimen collection, which can be used in accordance with the current invention. Non-cellulose DBS cards (Bond Elut DMS Card, Agilent Technologies, Santa Clara, Calif., USA) are also commercially available for DMPK research, which can be used in accordance with the present invention. They are claimed to be superior in form of improved mass spectrometry (MS) signal, less effort in punching and hematocrit independent spot homogeneity.

In contrast to conventional biological matrices, a fluid collection test strip provides a huge simplification in the arena of storage and transportation. Barring the humidity factor, which has significant influence on specimen stability and elevates the chances of bacterial growth, fluid collection test strip cards can be shipped and stored at ambient temperature. For protection from environmental humidity, fluid collection test strips can be wrapped and packed in sealed plastic bags with adequate desiccant and a humidity indicator to find out at what time the desiccant has to be replaced.

DBS cards are considered as non-regulated and exempt material as per US Department of Transportation (DOT) and the US postal service. Properly labelled DBS cards packets, which clearly convey the biohazardous nature of the content inside package to transportation personnel and other employees, can be shipped to analytical laboratories through mail, courier, or express mail delivery services. For establishing sample integrity and safety from occupational exposure of hazardous blood samples, basic triple packaging technology is used for DBS card shipment. Triple package comprises of primary container, secondary container, and a third covering of high quality paper envelope with an affixed or printed version of the international biohazard symbol. DBS packages can be stored at cool and dry place as such or can also be kept in polystyrene foam boxes until transportation to laboratories. If long-term stability of certain analytes at room temperature is not established on DBS cards, the packed DBS cards with desiccant can be stored in laboratory freezers until analysis to minimize analyte degradation.

A fluid collection test strip can be placed in a zip-lock bag or multi barrier pouch, put into a pre-stamped envelope and mailed to a remote location for analysis. Optionally, the fluid collection test strip can be air dried, e.g., for 15-30 minutes. This can be included in instructions of the back of the card if necessary. Results from the lab can be send to the user with the same barcode, for example, by mail, phone or in a mobile application or website. Dried fluid collection test strip can be punched out with various available diameter punching tools (manual, semi-automated, and automated). Punched dried cards can be used directly (by microfluidics) or by extraction of analytes with suitable extraction solvent. See, e.g., FIGS. 16-17. Extraction solvent should be optimized as per the solubility profile of the analyte(s) with consideration of minimizing extraction of interfering endogenous impurities. Extraction efficiency from fixed DBS can be improved by addition of liquid ammonium. After extraction, samples are subjected to analysis. Liquid chromatography, tandem mass spectrometry (LC-MS/MS), desorption electrospray ionization mass spectrometry (DESI-MS), gas chromatography-mass spectrometry (GC-MS), matrix assisted laser desorption mass spectrometry (MALDI-MS), MALDI time-of-fight mass spectrometry (MALDI-TOF-MS), high performance liquid chromatography (HPLC), isoelectric focusing (IEF)-HPLC, direct laser desorption (LD) TOF-MS, inductively coupled plasma mass spectrometry (ICP-MS), laser ablation (LA) ICP TOF-MS, polymerase chain reaction (PCR), enzyme linked immunosorbent assay (ELISA) and microfluidic chip have successfully been coupled with the DBS method for qualitative and quantitative analyses of blood samples. Commercial instruments are available for fully automated online DBS sampling and analysis. Online automated tools (ABS2; instech Solomon, Plymouth Meeting, Pa., USA and Culex; BASi, West Lafayette, Ind., USA) are capable of collecting blood from freely moving laboratory animals and can be coupled for serial sampling (in microlitre of blood volume) on DBS cards with high throughput and accuracy. Automated Sample Card and Prep (SCAP) system (Prolab, Reinach, Switzerland) can be coupled with LC-MS/MS for online drug analysis.

In one or more embodiments, a vaginal fluid collection kit includes a vaginal fluid collection system, e.g., the menstrual pad including the fluid collection strip as described herein above. The kit can optionally also return packaging (with instructions for the preparation and shipping of the DBS test card sample).

In one exemplary embodiment, the fluid collection test strip sample can be used for the detection of human papillomavirus (HPV). For the detection of HPV the DBS-pad is used and the DBS-card is sent for analysis at the lab. At the lab a small 1 cm×1 cm×1 mm or 1.5 cm×1.5 cm×1.5 mm piece of the DBS-card is punched out using sterile scissors or automated punching machines. Genomic DNA is extracted using commercial e.g. QIAamp DNA mini kit (catalog no. 51306; Qiagen, Hilden, Germany) according to the dried spot protocol. HPV DNA detection can be performed using two rounds of 50 cycles of PCR using the same set of My11 and My09 degenerate primers. Those primers are targeted at the conserved L1 region of the HPV genome, which allows detection of a broad range of HPV types. First-round PCR is performed using a reaction volume of 20 µl while 100 ng of DNA is used for each reaction. For the second-round PCR, 1 µl of the first-round PCR product is used in a reaction volume of 20 µl. β-Globin DNA detection should be performed for all samples as a housekeeping control using another pair of established primers. Reactions are performed in duplicate, and specific HPV types are confirmed by direct sequencing using the My11 primer. The sequencing products are analyzed using an ABI 3730x1 genetic analyzer (Applied Biosystems, Foster City, Calif.), and sequence homology can be examined by the use of the NCBI BLAST search program. Another method of detecting Human papilloma virus from the vaginal fluid collection test strip is to punch an area from the inlet with whole blood and put it into a solution of fixative such as but not limited to ThinPrep and put it onto a vortex machine. Finally an amount of the diluted vaginal fluid in the fixative can be analysed using GeneExpert. The sample could also be analysed using other detection machines such as roche and may require to be spun down as part of the protocol. Other protocols of HPV detection may also be used on the DBS-card.

For fluid collection test strips, other types of analysis can also be performed. This includes detection of regular health biomarkers such as Hemoglobin A1c, Lipo profile, Vitamins, Minerals, Hormones and other kinds of blood biomarkers. In other embodiments, the DBS test sample can be used to detect viruses and bacteria as well as other cancer types such as endometrial cancer and other cancer types that can be detected in blood. For the liquid menstrual blood sample in the menstrual cup with lid, the same biomarkers should be present for analysis however it will also be possible to look at cells and perhaps collect these for later use, e.g., stein cells have been shown as specifically interesting.

In one or more embodiments, the fluid collection system includes fluids collection test strip that can be removably integrated into a fluid adsorbent pad. In one or more embodiments, the fluid adsorbent pad can have the features of conventional feminine menstrual pads.

In other aspects, menstrual blood is collected using absorbent pads or other form factors that can be readily separated from the menstrual pad for shipping and remote analysis. In other embodiments, the DBS testing menstrual pad (the menstrual pad with a fluid collection strip) can also be incorporated into a panty liner, a tampon or a menstrual cup, as will be readily apparent to one of skill in the art.

FIG. 5C illustrates a DBS/DUS-detection card which detects and/or measures health markers using colorimetric detection methods 690. The detection card can be incorporated in feminine hygiene products or urine collection devices. The DBS/DUS-detection card can for this embodiment he made of paper which is coated with specific chemicals such as antibodies which through methods such as ELISA tests changes color once the analyte of interest is detected. It may employ lateral flow as illustrated in FIG. 5C but could alternatively be using vertical flow. The card may or may not have a cover as shown for the DBS-card in FIG. 5B. The DBS/DUS-detection card has inlets 691 which collects either the urine or vaginal fluid and leads it using capillary action (if lateral) gravity (if vertical) through a challenging system 693. In the channeling system 693 a specific location may be coated with a specific molecule (e.g. an antibody for a target antigen in the vaginal fluid). Once the vaginal fluid flows through the channels (if paper fluidics this will be due to capillary force) 693 and reaches and soaks the first reaction zone 692, antigens in the vaginal fluid binds to the antibodies, which have been put on this location. Because these are not immobilized, antibody-antigen molecules as well as antibodies, which have not reacted with antigens, will flow by capillary force to reaction zone 2, 694, where anti-antibodies are. These are not able to move and will bind to all the antibodies which has not reacted with an antigen. Only the antibody-antigen molecules will continue its flow to a third reaction zone, 695 where a colorimetric detection can take place. The color change will be shown on the card either in zone 3, 695. A control area to ensure enough fluid has run through the detection card may also be included. In this case much like a pregnancy test the user would have to see to lines of color change for the test to be positive. These details in the instructions will be clearly described on the back of the detection card.

FIG. 5D illustrates the same card as 5C but where the results are given immediately and interpreted using a mobile device. The camera of a device such as a mobile phone 698 takes a picture of the area where the colorimetric change has happened 695 and will using image analysis using pixel density 699 convert the color to a specific quantity of the analyte.

Figure 6:
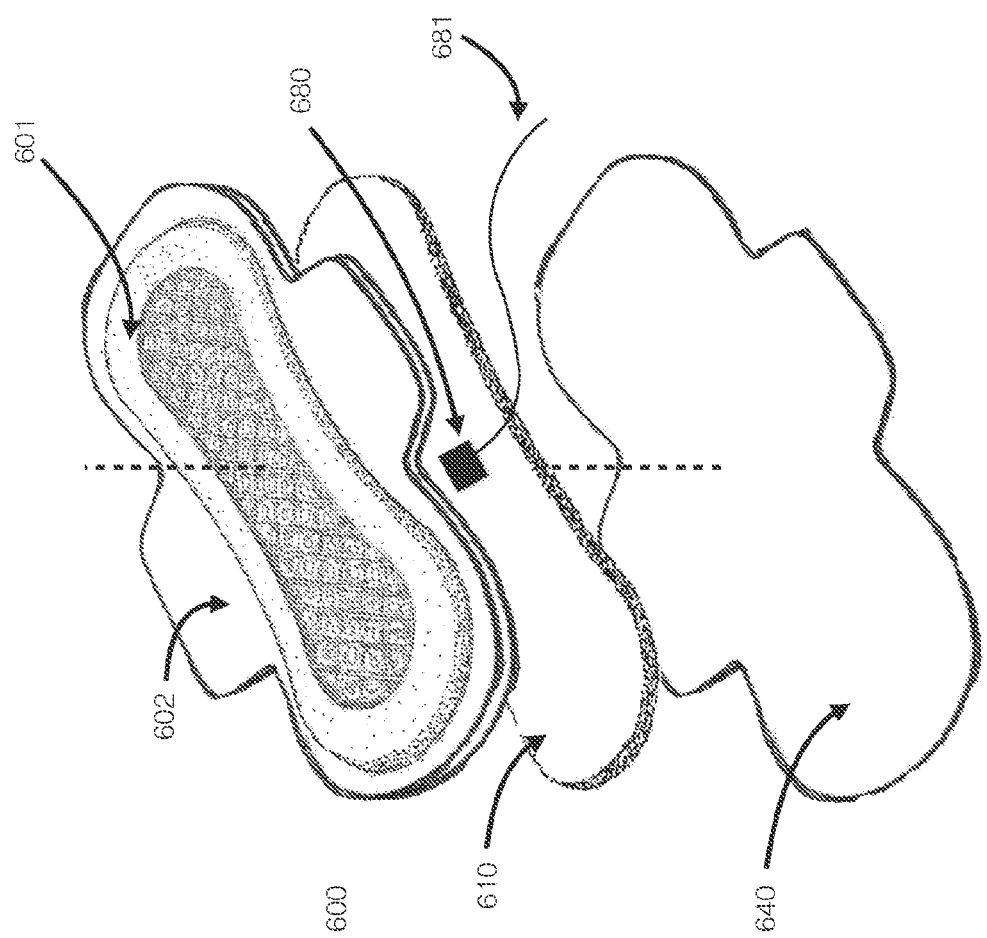
FIG. 6 illustrates a menstrual pad or panty liner with a pull string which takes a cube of the pad out according to one or more embodiments.

Other methods and devices for collection menstrual and/or vaginal fluids for analysis are contemplated. In one or more embodiments, an absorbent pad is a removable portion of the absorbent pad used to collect menstrual fluid during menses. The pad portion is readily separable from the feminine pad and can be equipped with a tab or string for easy removal. FIG. 6 illustrates a menstrual pad or panty liner where a pull string 681 can be pulled after usage and a cube of the pad 680 from the highly absorbent layer is pulled out and can be used for menstrual and vaginal fluid analysis.

Figure 11:
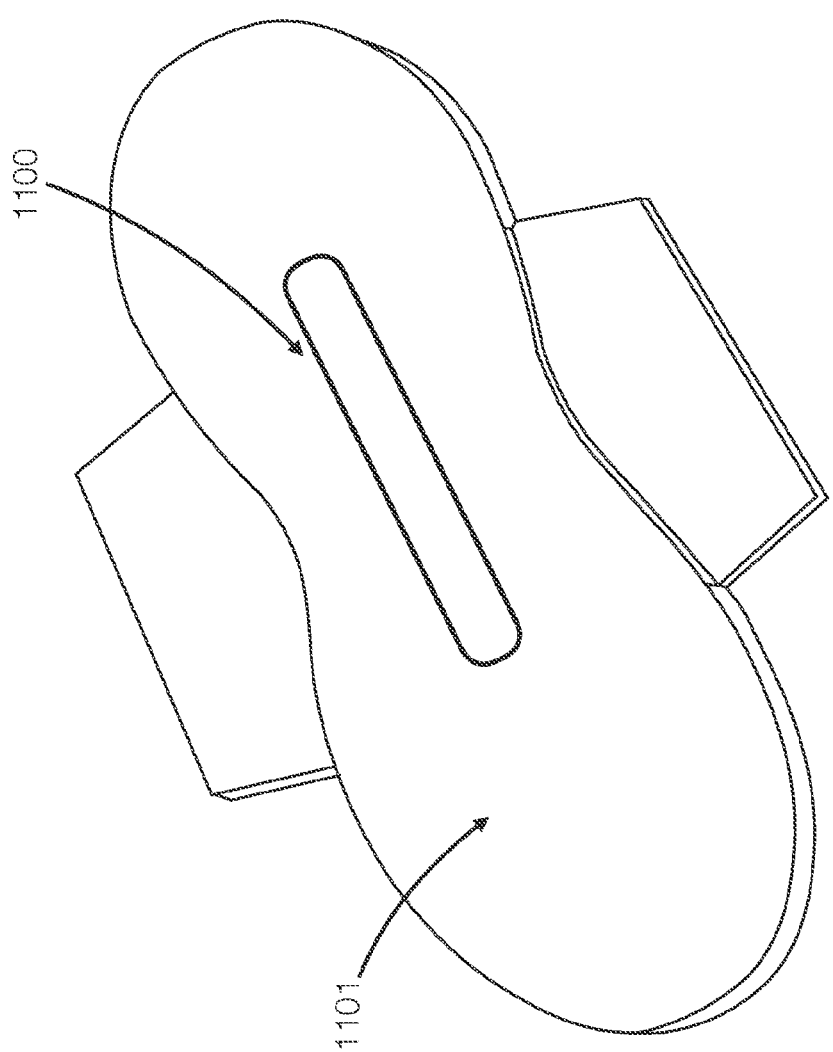
FIG. 11 is a menstrual pad, which has a strip on top of the top layer of the pad which can be peeled off and used for analysis.
Figure 12:
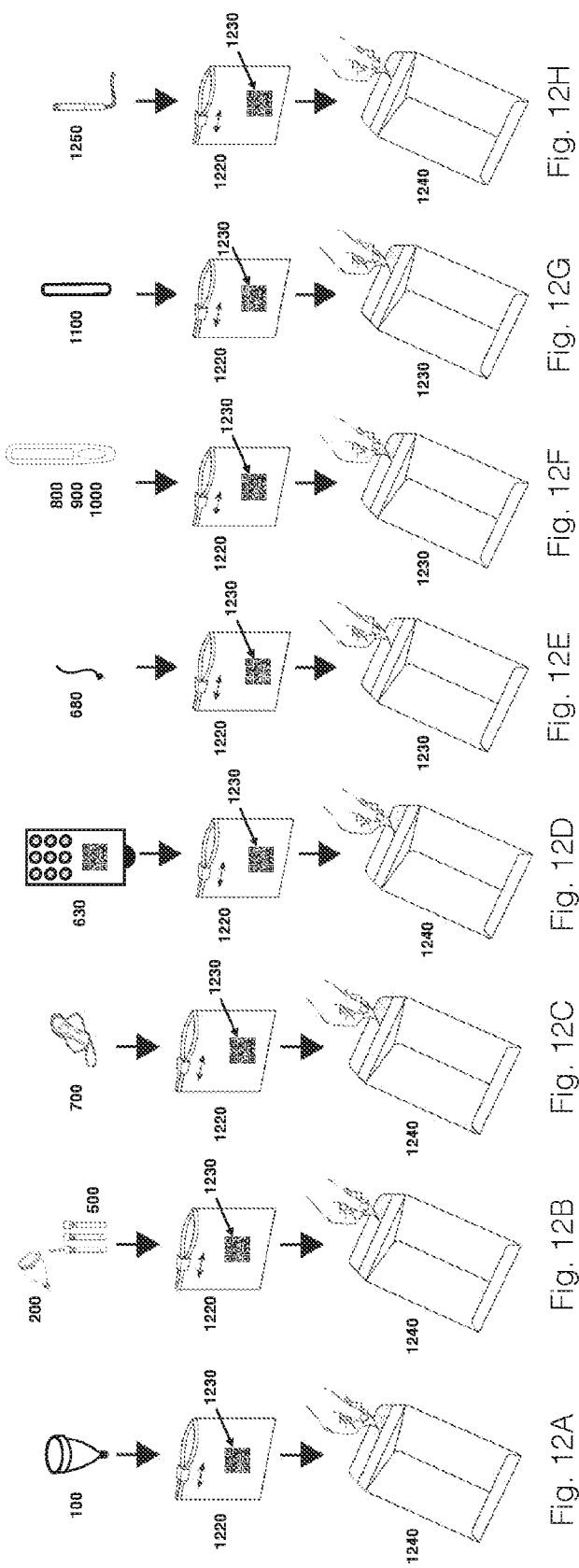
FIGS. 12A-12H illustrates different embodiments for a mail-in concept of various menstrual blood collection devices.

In one or more embodiments, the fluids collection test strip is an adsorbent removable strip that is secured or securable to a fluid adsorbent pad or menstrual pad. The fluids collection test strip can be peeled off after it has been soaked with menstrual or vaginal fluid. FIG. 11 is a menstrual pad which has a strip 1100 on top of the top layer 1101 of a menstrual pad. The strip 1100 can be peeled off after it has been soaked with menstrual or vaginal fluid. The strip 1100 may be a separate strip the user buys and puts on any pad she is already using, or it may already be located on a specific pad. The strip design could e.g. be any of the designs described in FIG. 8-10.

FIGS. 12A-12H illustrates how the menstrual cup with lid 100, collection tubes with menstrual blood 500, used menstrual-pads/panty liners 700, DBS-cards 630, square from highly absorbent pad pulled out with string 680, sample collection devices 800, 900, 1000 and 1100, or used tampons 1250 is put into a multi barrier pouch 1220. The multi barrier pouch functions as an air-secured container to preserve the menstrual blood sample from air and moisture so it may be used for blood analysis after transportation to a remote location. The multi barrier pouch 1220 could contain an oxidizer and a desiccant and can also be marked with a barcode or ID number 1230, which the can be used to track samples from users of the products, laboratory, biobanks or similar. The multi barrier pouch 1220, with 100, 500, 700, 710, 630, 680 or 800, 900, 1000, 1100, 1250 is closed and put into a pre-stamped envelope 1240, which is mailed to a specific remote location for analysis.

Figure 13:
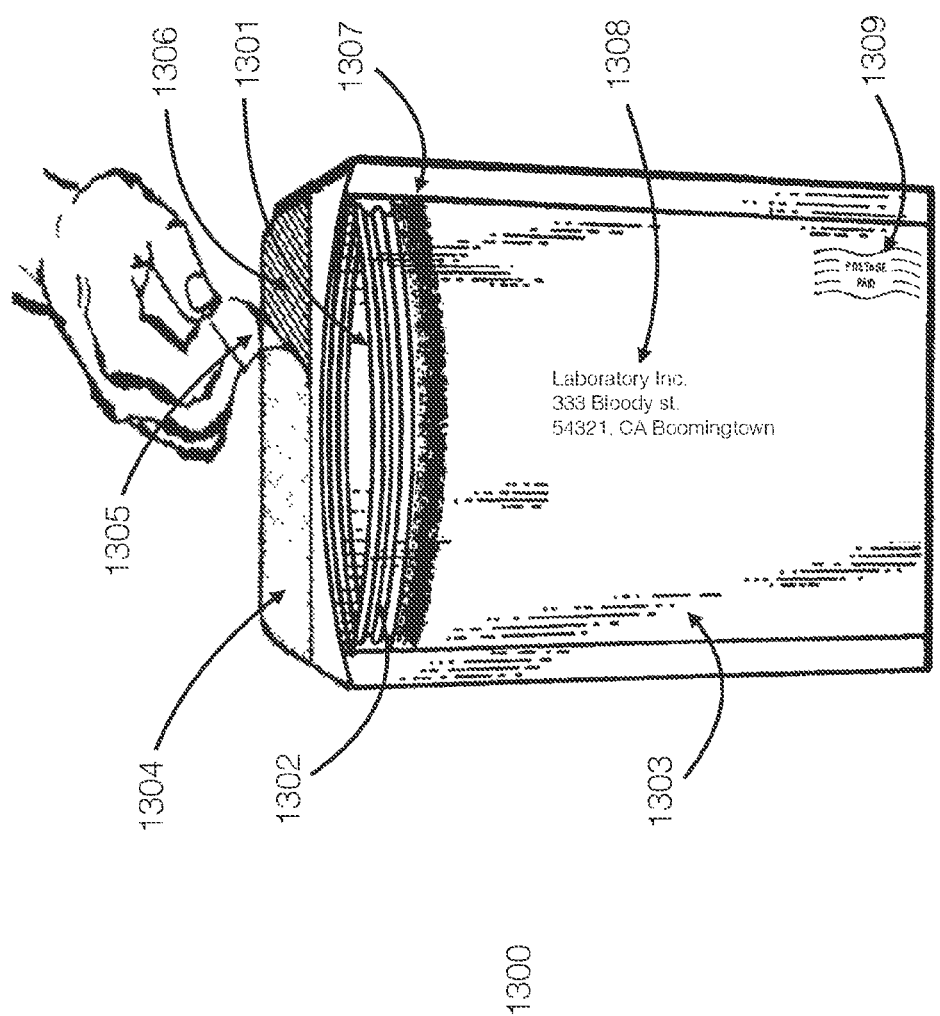
FIG. 13 illustrates a novel multi-barrier envelope a customized to fit mail-in requirements for dried blood spot samples.

FIG. 13 illustrates a 1300 multi barrier pouch married with an envelope. Once a specimen, such as 100, 500, 700, 710, 630, 680 or 800, 900, 1000, 1100, 1250 has been enclosed in the pouch, the opening 1301 of the pouch is sealed by sliding the rim 1302 together. The barriers of the pouch 1303 is made of three layers—an inner, middle and outer material. The three layers could be a made of thermoplastic materials such as e.g. rigid PVC, semi-rigid PVC, polycarbonate, acrylic, impact-modified acrylic, polystyrene, impact-modified polystyrene, ABS, polyethylene, polypropylene, and combinations thereof. As the pouch 1300 is sealed by closing opening 1303, a second closing method 1304 is activated by removing the release liner 1305 from the barrier, exposing a semi-strong adhesive 1306. The mechanism is closed by folding the barrier 1304 down on top of 1302, and sealed by the adhesive 1306 attaching to the outer part of the barrier 1307. As the multi barrier pouch 1300 is also an envelope, a pre-filled address 1308 is printed on the envelope and filed with pre-paid postage 1309 to be mailed to a laboratory for analysis.

Figure 14:
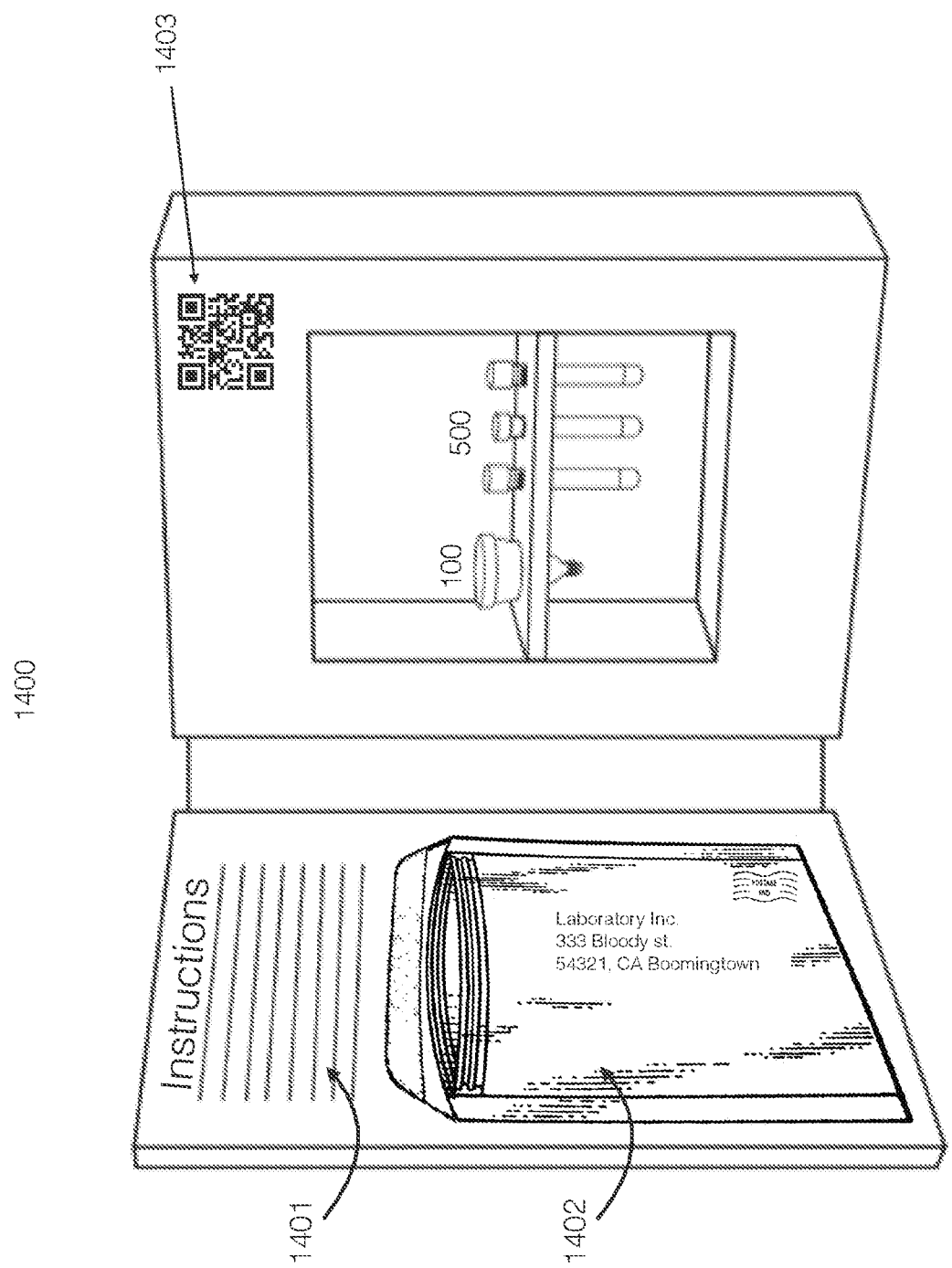
FIG. 14 is a customized collection kit for menstrual blood collection and mail-in a box according to one or more embodiments.

FIG. 14 illustrates a menstrual blood collection mail-in kit 1400. The different embodiments of menstrual blood collection shown in FIG. 1, 2A-E, 3, 4A-B, 5A-B, 6, 7, 8A-E, 9A-D, 10A-D, 11 can be delivered to the women with a full collection kit as illustrated here with vaginal fluid collection device 100 as the example. The kit can further consist of instruction manuals of e.g. how to use menstrual cups 200, how to seal the lid 300 on a system 100, guides to collect the samples in tubes if necessary, as well as instructions on how to use the fluid collection strip illustrated in FIGS. 7 to 11. The kit can also include regular menstrual pads, tampons and other menstrual blood collections devices, intended to be used in a mail-in procedure.

The kit can also consist of a multi barrier pouch 1402 such as 1220 or 1300 used for collection of 100, 500, 700, 710, 630, 680, 800, 900, 1000, 1100, 1250. If there is only a multi barrier pouch, an envelope with pre-postage stamps 1240 is also enclosed. The samples can then be sent in for remote analysis in a laboratory. The kit also has a unique ID 1403 that can he used to identify the kit, and be used to register online on a website, in an app or through a similar service.

Once a sample has been send via mail to a remote storage facility, the sample can be processed using both existing sample analysis methods already in use in commercial and clinical labs as well as new methods looking for unique biomarkers found in vaginal fluid.

The biomarkers which can be analyzed are the ones contained in menstrual blood and vaginal fluid. Specifically, for the fluid collection strips HR-HPV or any other strain of HPV are optimal, just as endometrial cancer, HIV viral loads, freefloating RNA or DNA is of interest. Other virus, bacteria or biomarkers such as vitamins, minerals, lipid profiles, hormone levels etc, in the blood can be analyzed and detected.

Figure 15:
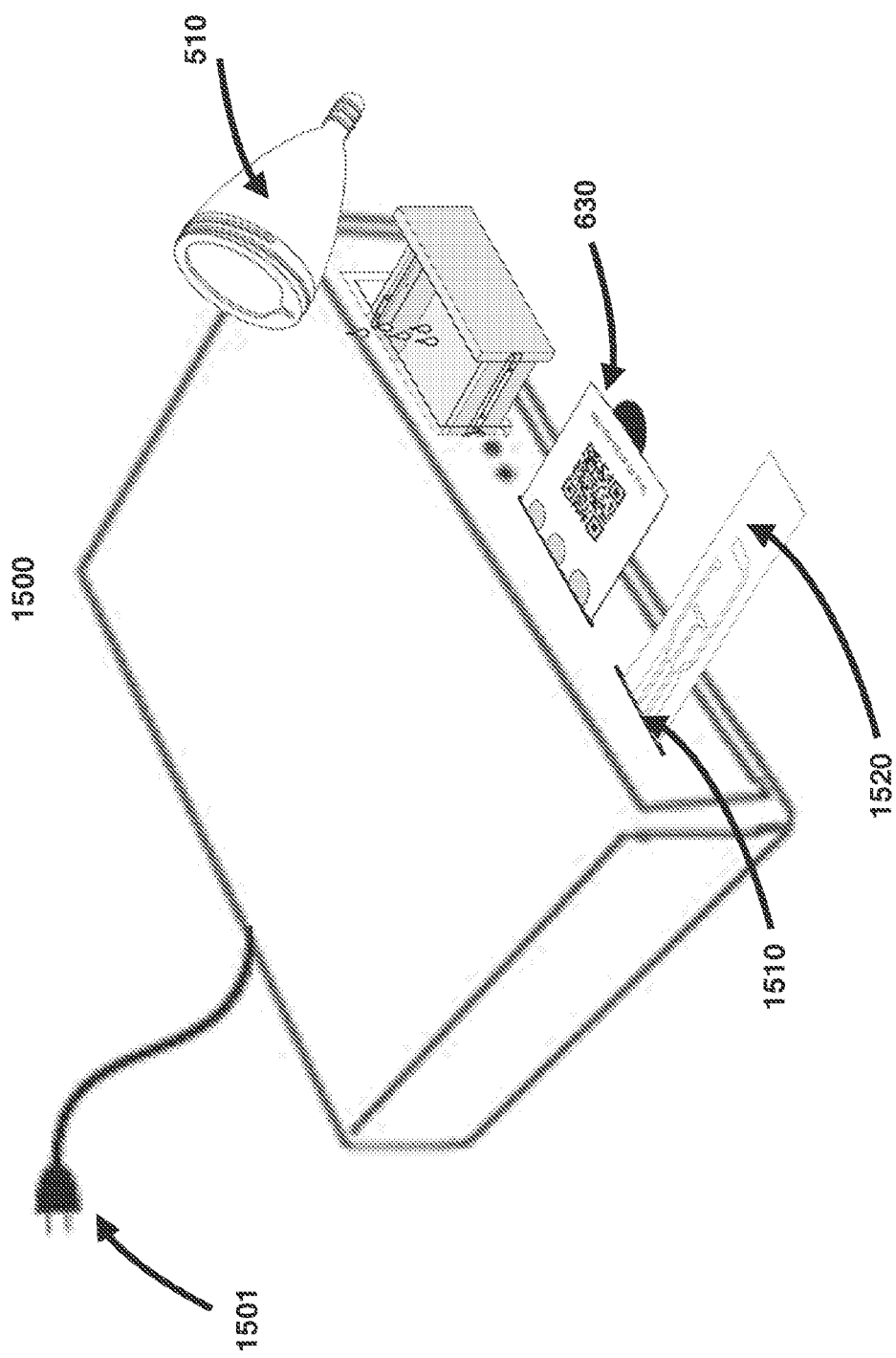
FIG. 15 is a home testing device which uses menstrual blood for analysis in at the point of care according to one or more embodiments.

FIG. 15 illustrates a device 1500 for home testing and analysis of menstrual blood or vaginal fluid. Instead of sending the samples 100, 500, 630, 680, 690, 800, 900,

1000, 1100 or 1250 to a remote location for analysis, a device for home usage as presented here may be ideal. The device has an opening 1510 in which a sample 1520 is inserted to using an intermediary device that can hold the sample, do sample preparation or control the volume inserted into the device. The device is specific for certain types of menstrual blood collections such as menstrual blood (as a fluid) from a menstrual cup such as 510, from fluid collection strips such as 800, 900, 1000, 1100, used tampon 1250, or electrochemical or optical biosensors as illustrated in 1520. The device may be able to process all different formats as illustrated in this embodiment. The device is specifically calibrated for menstrual blood and vaginal discharge. In the case of fluent sample use the device may also have a centrifuge function. Further the device employs a number of different blood analysis techniques including electrochemical testing, optical testing, polymerase chain reaction, mass spectrometry, chemical sequencing, chain-termination method, de novo sequencing for cutting or shearing larger DNA fragments, in vitro cloning to amplify individual DNA molecules, in vitro cloning, for amplifying individual DNA molecules. Methods such as next-generation sequencing can also be applied for genome sequencing, genome resequencing, transcriptome profiling (RNA-Seq), DNA-protein interactions (ChIP-sequencing), and epigenome characterization. These methods could be single-molecule real-time sequencing, ion semiconductor, pyrosequencing, sequencing by synthesis, sequencing by ligation or chain termination. Methods can also include massively parallel signature sequencing (MPSS), Polony sequencing, 454 pyrosequencing, SOLiD sequencing, DNA nanoball sequencing, heliscope single molecule sequencing, Nanopore DNA sequencing or RNAP sequencing. The data results from the analysis can be transmitted to a computer or phone or other similar devises via. USB cable or wirelessly through Bluetooth, GSM, Wi-Fi, RFID and other transmission techniques not illustrated in this figure. A power outlet 1501 which can be plugged into the wall can power the device. The device can also use a jack or mini jack which can be plugged into the phone to power the system and function as the transmission of data results.

FIG. 16A illustrates what happens once a vaginal fluid sample such as menstrual blood is introduced to a sample collection strip such as 1000. The illustration shows what a sample collection strip looks like after the protective cover 1001 has been removed. As the blood comes through the inlet 1012, it migrates down the paper 1020 and 1021. As both paper types in this example is filtration paper that can isolate plasma, the inlet 1012 will be soaked with larger cells such as red-blood cells. As the fluid travels laterally down the filtration paper 1020 and 1021, it will in plasma windows 1011 be visible as a more clear sample. The sample could here be e.g. blood plasma or other smaller cell types. As the sample arrives to the blood laboratory, either an automated system or a laboratory technician can punch or cut out a small sample from the sample collection strip 1000. FIG. 16B illustrates how samples 1601, 1602, 1603 and 1604 is punched out. In this example, 1602 is punched out from inlet 1012. If the sample paper 1020 has not been stabilized with e.g. a DNA preservative, the sample will have the same characteristics as a whole blood sample. In this example, 1601 is a pure plasma sample. Beneath the second inlet 1012 of the sample collection strip 1000, filtration paper 1021 is incorporated. The filtration paper may be coated with a DNA/RNA stabilizing agent, which will when sample 1603 and 1604 is punched out from the strip, be different from sample 1601 and 1602.

Figure 17C:
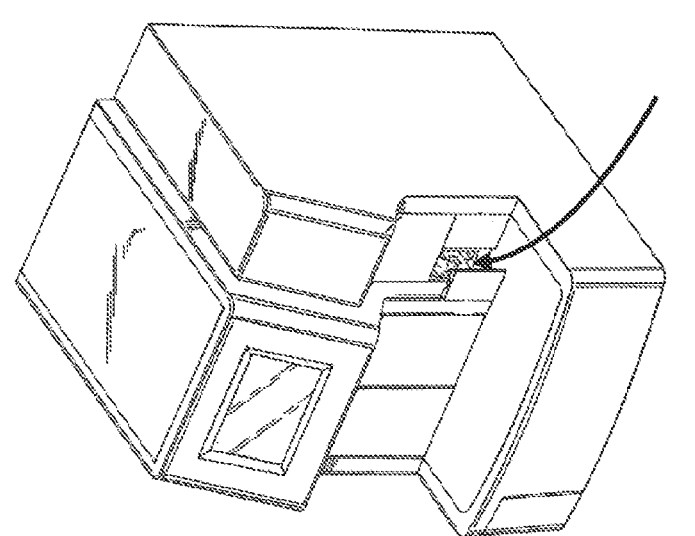
FIG. 17A-17C illustrates one embodiment of a laboratory process for sample extraction from the fluid collection strip, and analysis hereof.
Figure 17B:
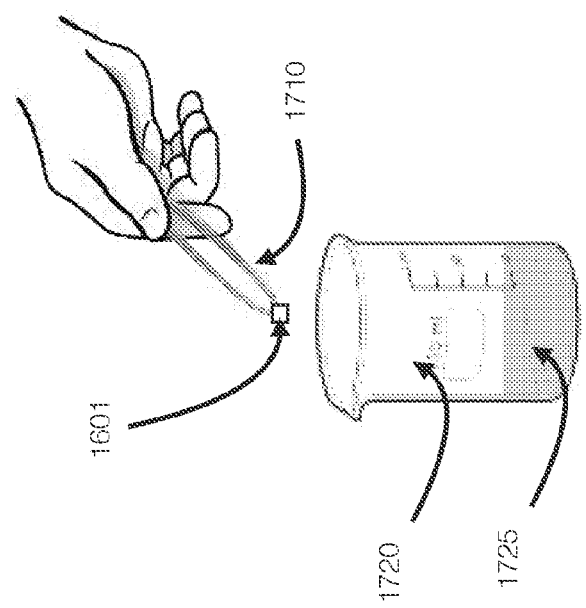
Figure 17A:
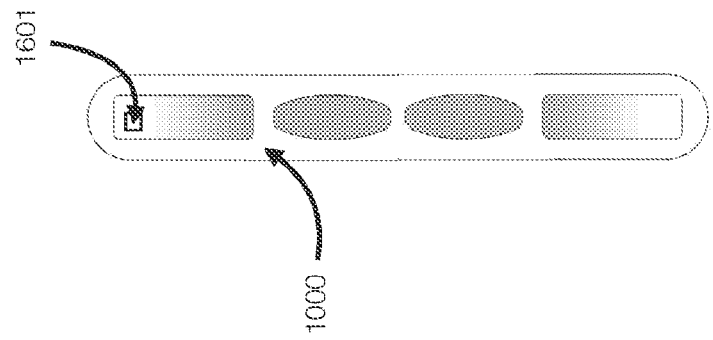

In FIG. 17A, 17B and FIG. 17C a laboratory process is illustrated. FIG. 17A illustrates how sample materials 1601 is punched out from the sample collection strip 1000. With a pincet 1710, a laboratory technician will in FIG. 17B introduce the sample 1601 into a volumetric flask 1720 with a pre-defined buffer material 1725. The buffer material can be a fixative or other required for processing the biomarker of interest. Once the sample 1601 has diluted into the buffer, it can be introduced to a chemical analyzer such as 1730.

Figures 18A, 18B, 18C:
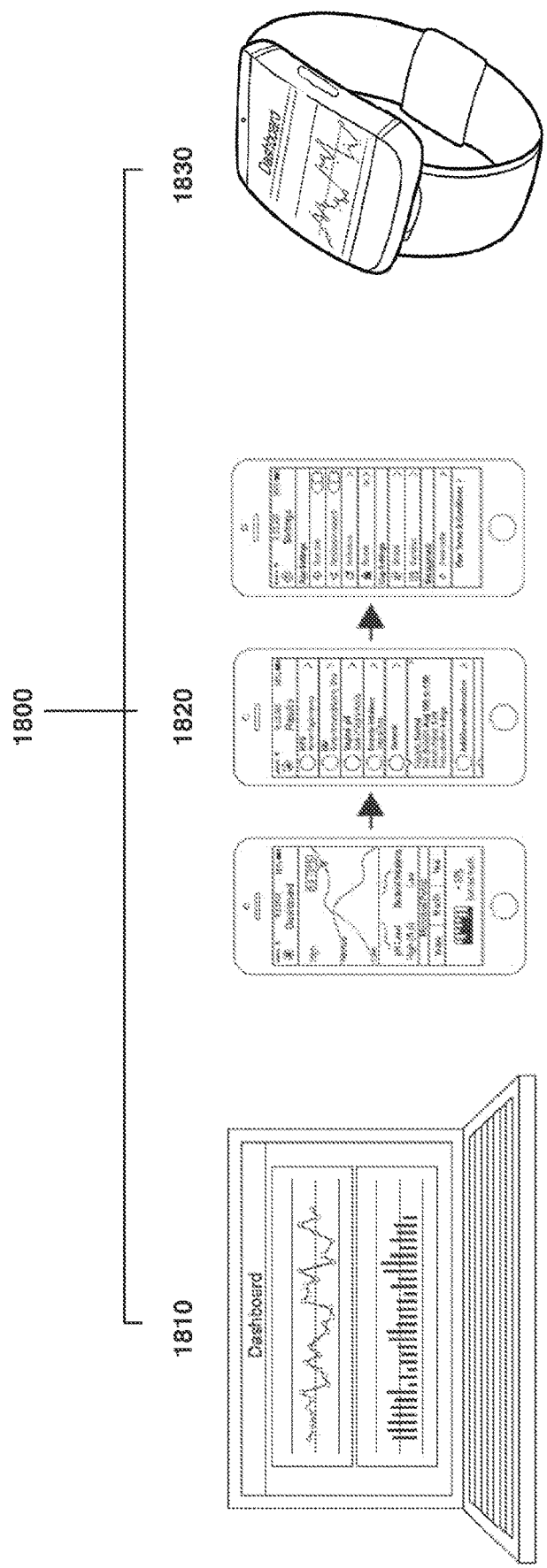
FIGS. 18A-18C exemplifies how data from an analysis can be displayed to a user on different embodiments of electronic devices according to one or more embodiments.

FIG. 18 exemplifies how data from an analysis can be displayed to a user on an electronic device 1800 such as a website or an app on a computer 1810, a handheld device such as a smartphone 1820 or on a smart-watch 1830. The data can also be displayed in other embodiments such as in glasses connected to the Internet, as audio through headphones, on a smart-mirror by the sink in a bathroom, or similar product categories. The data may be displayed with a number or a graph or similar. The data may be presented after interpretation from a health care professional or simply just as raw data. The data may also be displayed after data handling which is required for some biomarkers to translate biomarker level in menstrual blood to the equivalent in systemic blood.

Following are examples of data that the user can submit in the app/website: Name, Age, Location (through GPS or IP address), Home address, E-mail address, Password (to save their profile online), Pin code to access the app (if biometric functionality is used on a device, this can also be used). Credit card information to order testing or other services. The users can also input information about their menstrual cycle, and view their cycle in a calendar function. The calendar page can also display when a period is expected, or indicate when in the menstruation cycle the women is most likely to be fertile. This data can also be viewed as historical data, offering the user an opportunity to track her periods. Further a biomarker menu list from which biomarker analysis can he ordered and results viewed once laboratory has finished the analysis is available.

Figure 19:
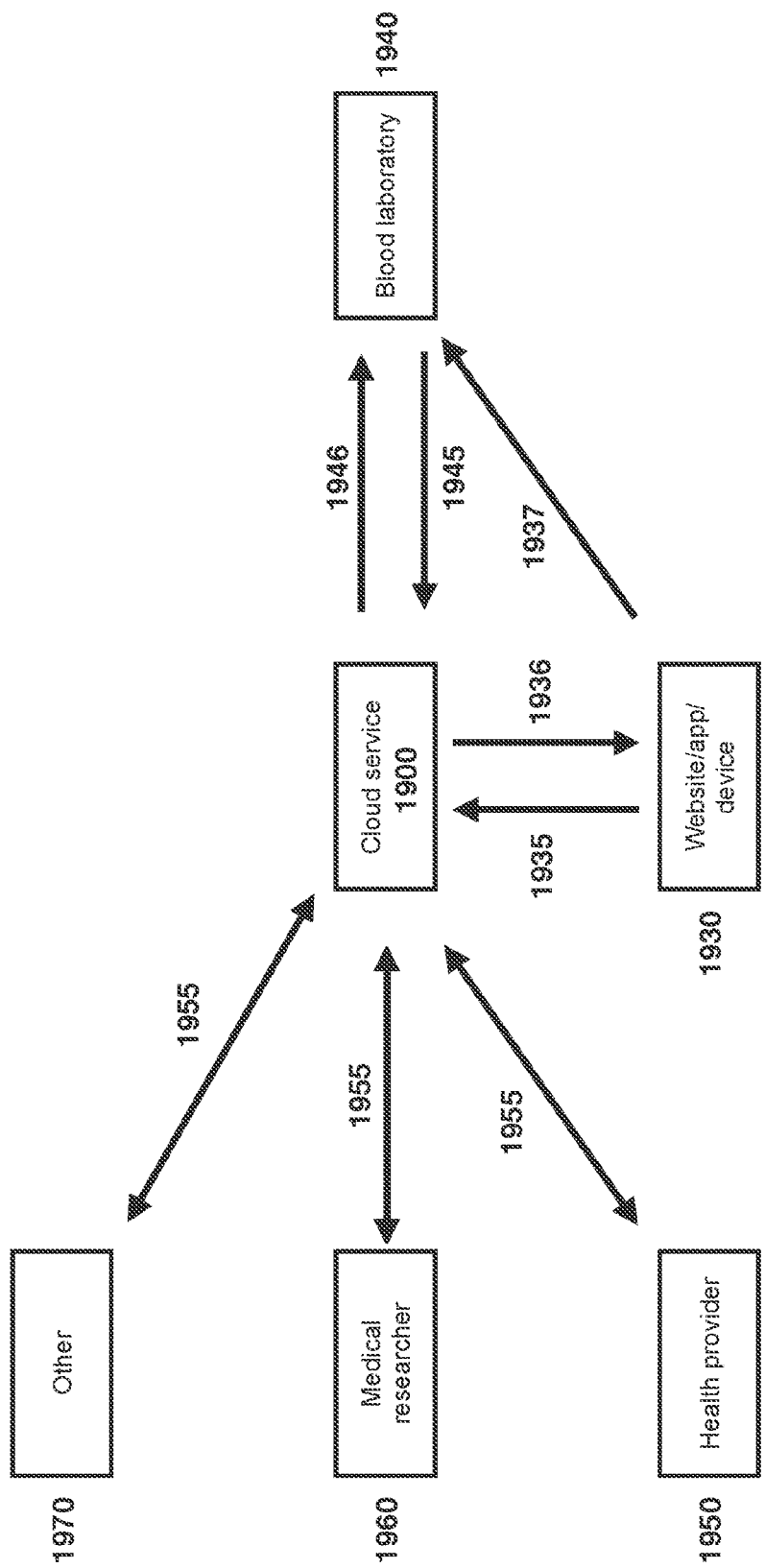
FIG. 19 is a process flow diagram illustrating the full information flow of the development of a remote blood analysis service according to one or more embodiments.

As illustrated in FIG. 19, the data collected in the app/website 1930 is encrypted and stored in a cloud service 1900. When a user receives a menstrual blood collection device such as 100, 200, 600, 680, 690, 800, 900, 1000 or 1100, the user registers the SN number 639 or a barcode 638 which may be labeled on the menstrual blood collection device, the multi barrier pouch, the mail-in kit 1400 or similar. Once registered the information is encrypted 1935 and stored in the cloud service 1900. After the user has used the medical device 100, 200, 600, 680, 690, 800, 900, 1000 or 1100 it is sent in an envelope 1240 or 1300 with mail 1937 to a blood laboratory 1940 for blood analysis. Once the blood sample is received at the blood laboratory 1940, the laboratory registers 1945 the sample in the cloud service 1900. After the blood laboratory 1940 has inputted the serial number into the cloud service, the details of which biomarkers should be analyzed will be available 1946 for the staff so blood analysis can be performed. Only the biomarker chosen by the user is available for the staff, which means any other information stored about the user specific to the SN number cannot be viewed. Once the laboratory has performed the analysis, results are encrypted and stored 1945 in the cloud 1900. In the cloud 1900, the encrypted results can now he sent 1936 back to the user. The cloud service 1900 also has an application program interface (API) 1955, through which other organizations can get specific access to information in the cloud 1930 and the results of a blood analysis. The API 1955 can have various permission levels, often controlled by the user, where e.g., health providers 1950 such as medical doctors, can get access to specific user information and blood results. It is also possible to give limited access to e.g. medical researchers 1960 or other providers 1970 such as insurance companies. In some embodiments, a digital service can aggregate the cumulative, collected results of a menstrual fluid analysis. The aggregated data can provide an opportunity to find new information from the total amount of fluid analysis.

It will be appreciated by those skilled in the art that the invention can take many forms, and that such forms are within the scope of the invention as claimed. Therefore, the spirit and scope of the appended claims should not be limited to the descriptions of the preferred versions contained herein.

The invention claimed is:

1. A vaginal fluid collection system comprising:
   a fluid pervious top face sheet;
   a fluid impervious backing sheet;
   an absorbent pad disposed between the face sheet and backing sheet; and
   a fluid collection test strip having a grippable portion extending from an edge of the strip, the fluid collection test strip disposed in fluidic contact with the absorbent pad;
   wherein at least one of the backing sheet or the top face sheet comprises an opening sized to allow at least one of the removal and insertion of the fluid collection test strip from the fluid collection system.

2. The collection system of claim 1, wherein the grippable portion is disposed in the top face opening.

3. The collection system of claim 1, wherein the grippable portion is disposed in the backing sheet opening.

4. The collection system of claim 1, wherein the fluid collection test strip is disposed between the top face sheet and the absorbent pad.

5. The collection system of claim 4, wherein the fluid collection test strip is disposed in a recess defined in the absorbent pad.

6. The collection system of claim 4, wherein the fluid collection test strip is disposed in a pocket located on the absorbent pad.

7. The collection system of claim 6, wherein the pocket is comprised of the top face sheet selectively adhered and non-adhered to the absorbent pad to define the pocket.

8. The collection system of claim 6, wherein the pocket comprises the opening sized to allow at least one of the removal and insertion of the fluid collection test strip.

9. The collection system of claim 1, wherein the fluid collection test strip comprises a fluid absorbing layer disposed between upper and lower protective layers, the upper and lower protective layers comprising at least one opening, wherein said at least one opening is positioned to provide fluidic contact with the absorbent pad.

10. The collection system of claim 9, further comprising a fluid impervious layer disposed between the upper protective layer and the fluid absorbing layer, the fluid impervious layer comprising at least one opening to allow fluid flow to the fluid adsorbing layer.

11. The collection system of claim 10, wherein at least one of the upper and lower protective layers and the fluid impervious layer, when present, comprise a plurality of openings.

12. The collection system of claim 9, wherein the fluid adsorbing layer comprises a plurality of fluid adsorbing zones.

13. The collection system of claim 12, wherein the plurality of fluid adsorbing zones are fluidically isolated from one another and in fluidic communication with different openings in the upper and lower protective layers.

14. The collection system of claim 9, wherein the fluid adsorbing layer comprises at least one whole blood test strip.

15. The collection system of claim 9, wherein the fluid adsorbing layer comprises at least one plasma-separating test strip.

16. The collection system of claim 1, wherein the fluid collection test strip is at least one of coated and selected to have a pore size suitable to filter blood cells.

17. The collection system of claim 9, wherein the fluid adsorbing layer comprises at least one plasma-separating test strip and at least one whole blood test strip.

18. The collection system of claim 17, wherein the plurality of test strips are in the same layer.

19. The collection system of claim 1, wherein the fluid collection test strip comprises a non-adsorbent sheet having at least one fluid adsorbent region in fluidic communication with the adsorbent pad.

20. The collection system of claim 1, wherein the fluid collection test strip comprises a color indicator selected to provide a visual indication of the presence of a biomarker in a vaginal fluid.

21. The collection system of claim 20, wherein the color indicator is readable using a mobile device or other electronic reader.

22. The collection system of claim 1, wherein the fluid collection test strip comprises a computer readable identifier, RFID or other kind of ID.

23. The collection system of claim 1, further comprising packaging for use in shipping the fluid collection test strip or components thereof.

24. The collection system of claim 23, wherein the packaging comprises an envelope having a multi-barrier pouch integrally inserted into the envelope.

25. The collection system of claim 1 further comprising:
   a fluid absorbing layer disposed between upper and lower protective layers, the upper and lower protective layers comprising at least one opening, wherein said at least one opening is positioned to provide fluidic communication to the fluid absorbing layer and the fluid adsorbing layer comprising a plasma-separating test strip;
   a fluid impervious layer disposed between the upper protective layer and the fluid absorbing layer, the fluid impervious layer comprising a first opening to allow fluid flow to the fluid adsorbing layer and a second opening defining a window for viewing separated plasma.

26. The collection system of claim 25, wherein the upper and lower protective layers comprise a plurality of openings.

27. The collection system of claim 25, wherein the fluid adsorbing layer comprises a plurality of fluid adsorbing zones.

28. The collection system of claim 27, wherein the plurality of fluid adsorbing zones are fluidically isolated from one another and in fluidic communication with different openings in the upper and lower protective layers.

29. The collection system of claim 25, wherein the fluid adsorbing layer comprises at least one plasma-separating test strip and at least one whole blood test strip.

30. The collection system of claim 25, wherein the fluid adsorbing layer comprises two plasma-separating test strips.

31. The collection system of claim 25, wherein the fluid collection test strip comprises a color indicator selected to provide a visual indication of the presence of a biomarker in a vaginal fluid.

32. The collection system of claim 25, wherein the fluid collection test strip comprises a computer readable identifier, RFID or other kind of ID.

33. The collection system of claim 1 further comprising:
- a fluid receptacle having an open top end and extending to a closed bottom end and an optional stem attached to the receptacle at the bottom end thereof, the receptacle having an inner wall and an outer wall and a rim extending circumferentially around the open top end; and
- a lid dimensioned to fit on the rim of the open top end of the receptacle, the lid having an upper surface and a lower surface, wherein the cap and the rim of the receptacle are dimensioned and arranged to engage to form a fluid tight seal.

34. The collection system of claim 33, comprising complementary threaded grooves on the lid and the rim of the receptacle.

35. The collection system of claim 33, comprising depressions or slots located on the rim of the receptacle and protrusions located on a circumference of the lid, wherein the protrusions are capable of engagement with the depressions.

36. The collection system of claim 33, wherein the lid and rim of the receptacle comprise a ball and socket mechanism.

37. The collection system of claim 33, wherein the sealing mechanism comprises a snap-fit mechanism.

38. The collection system of claim 33, wherein the lid can include an adhesive backed sheet positionable to form an adhesive seal with the receptacle rim.

39. The collection system of claim 33, further comprising an additive.

40. The collection system of claim 39, wherein the additive is an anti-coagulant, preservative or antibiotic or other chemicals which may be used for the diagnostic assay or to lyse cells.

41. The collection system of claim 39, wherein the additive coats at least one of the inner wall of the cup and the lower surface of the lid.

42. The collection system of claim 39, wherein the additive is a fluid or solid housed within the receptacle.

43. The collection system of claim 39, comprising a container housing the additive separate from the receptacle.

44. The collection system of claim 33, further comprising a collection tube for storage of a vaginal fluid.

45. The collection system of claim 44, wherein the collection tube houses an additive.

46. The collection system of claim 45, wherein the additive is at least one of an anti-coagulant, preservative, antibiotic and other chemicals for preservation of vaginal fluid or useful in the diagnostic chemical processes.

47. The collection system of claim 45, wherein the additive coats the inner wall of the collection tube.

48. The collection system of claim 45, wherein the additive is a fluid or solid housed within the collection tube.

49. The collection system of claim 33, wherein at least one of the receptacle and the lid comprises a computer readable identifier, RFID or any other kind of ID.

50. The collection system of claim 49, further comprising packaging for use in shipping the sealed menstrual cup or the collection tube.

\* \* \* \* \*